United States Patent [19]

Matsumoto et al.

[11] Patent Number: 4,845,097
[45] Date of Patent: Jul. 4, 1989

[54] PHENOXYALKYLAMINOPYRIMIDINE DERIVATIVES AND INSECTICIDAL AND ACARICIDAL COMPOSITIONS CONTAINING THEM

[75] Inventors: Keigo Matsumoto; Shinji Yokoi, both of Shiga; Katsutoshi Fujii, Ube, all of Japan

[73] Assignees: Sankyo Company Limited, Tokyo; UBE Industries Limited, Ube, both of Japan

[21] Appl. No.: 839,777

[22] Filed: Mar. 14, 1986

[30] Foreign Application Priority Data

Mar. 14, 1985 [JP] Japan ................................. 60-51307
Jun. 14, 1985 [JP] Japan ................................. 60-128344

[51] Int. Cl.⁴ .................. A01N 43/54; C07D 239/70; C07D 413/10
[52] U.S. Cl. ................................. 514/234.2; 544/326; 544/327; 544/328; 544/253; 544/278; 544/293; 544/122; 544/123; 544/119; 514/258; 514/259; 514/256; 514/234.5; 514/235.8
[58] Field of Search ............... 544/326, 327, 328, 253, 544/278, 293, 122, 123, 119; 514/258, 259, 256, 234.2, 234.5, 235.8

[56] References Cited

U.S. PATENT DOCUMENTS 4,213,987  7/1980  Nakagami et al. .................. 544/326
4,435,402  3/1984  Tsuji et al. ......................... 544/326
4,562,193 12/1985  Yamamoto et al. ................. 544/326

FOREIGN PATENT DOCUMENTS 086099  7/1982  Japan ................................. 544/326
 36667  2/1984  Japan ................................. 544/326

*Primary Examiner*—Richard A. Schwartz
*Assistant Examiner*—Robert C. Whittenbough
*Attorney, Agent, or Firm*—Frishauf, Holtz, Goodman & Woodward

[57] ABSTRACT

Compounds of formula (I):

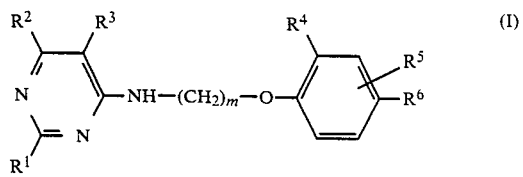

(where $R^1$–$R^5$ are various conventional atoms or groups, m is 2 or 3 and $R^6$ is an optionally substituted alkoxyalkyl, alkylthioalkyl, alkylaminoalkyl or heterocyclic-substituted alkyl group or $-CH_2-CH=NOR^7$ where $R^7$ is hydrogen, alkyl, alkenyl or aralkyl) have insecticidal and acaricidal activities.

43 Claims, No Drawings

PHENOXYALKYLAMINOPYRIMIDINE DERIVATIVES AND INSECTICIDAL AND ACARICIDAL COMPOSITIONS CONTAINING THEM

BACKGROUND OF THE INVENTION

The present invention relates to a series of new phenoxyalkylaminopyrimidine derivtives which have valuable insecticidal and acaricidal activities and also provides processes for preparing these derivatives and compositions containing them as the active ingredient.

Insects and acarids cause considerable damage to plants and can represent a serious danger to health; at best, they are a major nuisance. Accordingly, large sums are spent to destroy or deter them. Although many insecticides and acaricides are available, a large number of these have to be used with care, because they can endanger animals or because of their phytotocicity. Moreover, because insects and acarids have short life cycles, they can develop immunity to many of the commonly used insecticides and acaricides, and, accordingly, there is always a continuing need for new compounds exhibiting insecticidal and acaricidal properties.

A number of phenoxyalkylamine derivatives is known, e.g. from U.S. Pat. Nos. 4,213,987, 4,435,402 and 4,562,193. These known compounds can, broadly speaking, be represented by the formula:

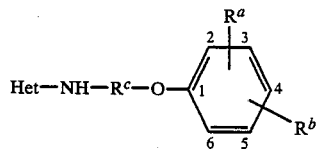

in which:
R$^a$ and R$^b$ each represent alkyl groups;
R$^c$ represents an alkylene group; and
Het represents a heterocyclic ring system, for example a pyrimidine ring or a pyrimidine ring fused to another ring, e.g. fused to a benzene ring (to form a quinazoline ring) or fused to a cycloalkane or thiophene ring, and, of course, such rings are optionally substituted.

Such compounds have insecticidal and acaricidal activities and are effective for the eradication of various noxious insects and mites which are problems in agriculture or horticulture, for example the diamondback moth (*Plutellae xylostella*), aphids, the two-spotted spider mite (*Tetranychus urticae*) and the citrus red mite (*Panonychus citri*).

We have now found that a class of compounds similar to the known ones described above, but which have a highly specific class of substituted alkyl groups at the 4-position of the phenyl group in the formula shown above, have insecticidal and acaricidal activities far superior to those of the known compounds, and, in particular, they have superb acaricidal activity.

BRIEF SUMMARY OF THE INVENTION

The compounds if the invention are those compounds of formula (I):

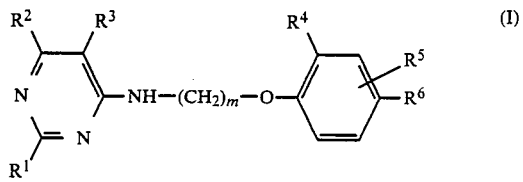

in which:
R$^1$ represents a hydrogen atom, a C$_1$–C$_4$ alkyl group or a halogen atom;
R$^2$ and R$^3$ are independently selected from the group consisting of C$_1$–C$_4$ alkyl groups, halogen atoms, C$_2$–C$_4$ alkoxyalkyl groups, C$_2$–C$_4$ alkylthioalkyl groups and C$_3$ and C$_4$ cycloalkyl groups, or R$^2$ and R$^3$ together represent, with the carbon atoms to which they are attached, a 5- or 6-membered ring which is a carbocyclic ring or is a heterocyclic ring containing a single oxygen or sulfur hetero-atom, the ring being unsubstituted or having 1 or 2 substituents selected from the group consisting of C$_1$–C$_4$ alkyl groups and halogen atoms;
m is 2 or 3;
R$^4$ and R$^5$ are independently selected from the group consisting of hydrogen atoms, C$_1$–C$_4$ alkyl groups and halogen atoms; and
R$^6$ represents a group of formula —A—B—(-DO)$_n$—E, where
A represents a C$_1$–C$_8$ alkylene group or a C$_1$–C$_8$ alkylene group having a single C$_1$–C$_4$ alkoxy substituent;
B represents an oxygen atom (—O—), a sulfur atom (—S—) or an imino group (—NH—);
D represents a C$_1$–C$_6$ alkylene group or an alkyleneoxyalkylene group where each alkylene part is C$_1$–C$_4$;
n is 0 or 1; and
E represents a C$_1$–C$_6$ alkyl group, a C$_3$–C$_6$ alkenyl group, a C$_4$–C$_6$ alkadienyl group, a C$_3$ or C$_4$ alkynyl group or an aralkyl group having from 7 to 9 carbon atoms;
or a group of formula —CH$_2$—W, where:
W represents a group of formula —CH=N—OR$^7$ where R$^7$ represents a hydrogen atom, a C$_1$–C$_4$ alkyl group, a C$_3$ or C$_4$ alkenyl group or a C$_7$–C$_9$ aralkyl group,
a morpholinomethyl group or a heterocyclic group having from 5 to 8 ring atoms, of which 2 or 3 are hetero-atoms selected from the group consisting of oxygen and sulfur hetero-atoms, said heterocyclic ring being saturated or having a single unsaturated bond in its ring, and said ring being unsubstituted or having one or two substituents selected from the group consisting of C$_1$–C$_4$ alkyl groups, C$_1$–C$_4$ haloalkyl groups, phenyl groups and oxygen atoms;
and acid addition salts thereof.

The invention also provides an agrochemical composition comprising an insecticidal and acaricidal agent and a carrier therefor, wherein said insecticidal and acaricidal agent is selected from the group consisting of compounds of formula (I) and acid addition salts thereof.

The invention further provides a method of protecting plants from insect and acarid attack, comprising applying to the site of said plants an agricultural composition which contains as an active ingredient an insecticidally and acaricidally effective amount of a compound of formula (I) or acid addition salt thereof.

The invention also provides processes for preparing the compounds of the invention, as defined in more detail hereafter.

DETAILED DESCRIPTION OF INVENTION

Where $R^1$, $R^2$, $R^3$, $R^4$, $R^5$, $R^7$ or the substituents on the ring represented by $R^2+R^3$ or on the heterocyclic ring represented by W are $C_1-C_4$ alkyl groups, these may be straight or branched chain groups and examples include the methyl, ethyl, propyl, isopropyl, butyl, isobutyl, sec-butyl and t-butyl groups.

Where $R^1$, $R^2$, $R^3$, $R^4$, $R^5$ or the substituents on the ring represented by $R^2+R^3$ is a halogen atom, this may be a chlorine, bromine, fluorine or iodine atom.

Preferably, $R^1$ represents a hydrogen atom or a methyl group.

Where $R^2$ or $R^3$ represents a $C_2-C_4$ alkoxyalkyl or alkylthioalkyl group, the alkoxy and alkyl parts may be straight or branched chain groups, but are preferably straight chain groups and examples include the methoxymethyl, ethoxymethyl, propoxymethyl, 2-methoxyethyl, 2-ethoxyethyl, 3-methoxypropyl, methylthiomethyl, ethylthiomethyl, propylthiomethyl, 2-methylthioethyl, 2-ethylthioethyl and 3-methylthiopropyl groups.

Where $R^2$ or $R^3$ represents a $C_3$ or $C_4$ cycloalkyl group, this is a cyclopropyl or cyclobutyl group.

Where $R^2$ and $R^3$, together with the carbon atoms to which they are attached, form an additional 5- or 6-membered ring, this may be a carbocyclic ring or it may be a heterocyclic ring containing a single oxygen or sulfur atom, the carbocyclic or heterocyclic ring being fused to the pyrimidine ring via the 5- and 6-carbon atoms of the pyrimidine ring. Apart from the carbon atoms through which the fusion occurs, the remaining atoms of the ring formed by $R^2$ and $R^3$ may be saturated or unsaturated and the resulting ring may be fully unsaturated or only partially unsaturated. Examples of preferred rings which may be formed by $R^2$, $R^3$ and the fusion carbon atoms of the pyrimidine ring include cyclopentene rings, cyclohexene rings, cyclohexadiene rings, benzene rings, thiophene rings and furan rings. In particular, we prefer that the part of the compound of formula (I) represented by the partial formula (I'):

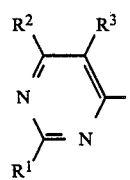

should be represented by any one of the partial formulae (Ia)-(Ih):

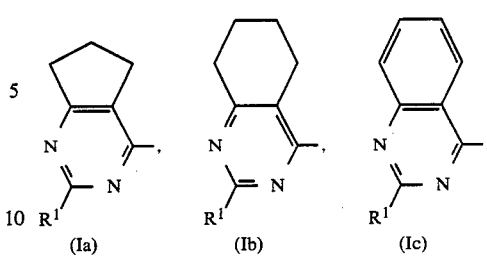

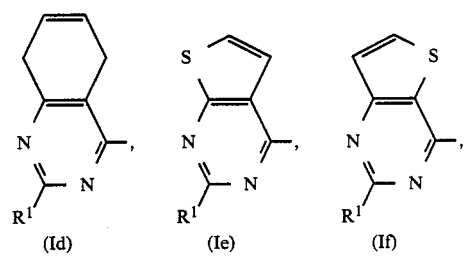

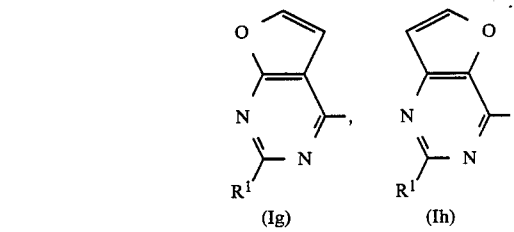

(in which $R^1$ is as defined above).

The ring fused onto the pyrimidine ring in these partial formulae may be unsubstituted or may have one or two substituents selected from the group consisting of $C_1-C_4$ alkyl groups and halogen atoms, and examples of such substituents include the groups and atoms heretofore exemplified.

Preferably one of $R^2$ and $R^3$ (preferably $R^2$) is a methyl or ethyl group and the other is a chlorine or bromine atom, or they, together with the pyrimidine ring, form one of the partial formulae (Ia)-(Ih) shown above which are unsubstituted or, where substituted, in the case of formulae (Ia)-(Id) have one or two methyl, chlorine or fluorine substituents or in the case of formulae (Ie)-(Ih) have one or two methyl substituents.

m is preferably 2.

A represents an alkylene group, that is to say a divalent saturated aliphatic hydrocarbon group. The two valencies by which the alkylene group A is attached, on the other hand, to the benzene ring and, on the other hand, to the atom or group represented by B may be on the same or different carbon atoms; where such valencies are present on the same carbon atoms, the groups are sometimes referred to as "alkylidene" groups, as a sub-class of alkylene groups. The alkylene group represented by A may be a straight or branched chain group and has from 1 to 8 carbon atoms. Examples of such groups include the methylene, ethylene, ethylidene, trimethylene, 1-methylethylene, 2-methylethylene, propylidene, dimethylmethylene, tetramethylene, 1,1-dimethylethylene, 1,2-dimethylethylene, 2,2-dimethylethylene, 1-ethylethylene, 2-ethylethylene, pentamethylene, 1-propylethylene, 2-propylethylene, 1,1,2-trimethylethylene, 1-methyl-2-ethylethylene, hexamethylene, heptamethylene, octamethylene, 1-ethylhexamethylene and 2-ethylhexamethylene groups. Such an alkylene group represented by A may be unsubstituted or can have a single $C_1$-$C_4$ alkoxy substituent, which itself may be a straight or branched chain group, for example a methoxy, ethoxy, propoxy, isopropoxy, butoxy or isobutoxy group. We particularly prefer that A should represent a $C_1$-$C_5$ alkylene group or a $C_1$-$C_5$ alkylene group having a single methoxy substituent, and most preferably it is an unsubstituted $C_1$-$C_5$ alkylene group.

D can represent a $C_1$-$C_6$ alkylene group or an alkyleneoxyalkylene group in which each alkylene part is $C_1$-$C_4$, preferably $C_1$-$C_3$. The alkylene groups and alkylene parts of the alkyleneoxyalkylene groups may be those $C_1$-$C_6$ and $C_1$-$C_4$ groups exemplified above in relation to A, but preferred examples of groups which may be represented by D include the —$CH_2$—, —($CH_2$)$_2$—, —($CH_2$)$_3$—, —($CH_2$)$_4$—, —$CH_2OCH_2$—, —$CH_2O(CH_2)_2$—, —($CH_2$)$_2OCH_2$—, —($CH_2$)$_2O(CH_2)_2$— and —($CH_2$)$_3O(CH_2)_3$— groups.

B represents an oxygen or sulfur atom or an imino group, preferably at oxygen atom or an imino group, and the group of formula —B—(DO)$_n$— is preferably an oxygen atom, a sulfur atom, an imino group or a group of formula —NH—($CH_2$)$_2$—O—, —O—($CH_2$)$_p$—O— or —O—($CH_2$)$_q$—O—($CH_2$)$_q$—O— (in which p represents an integer from 1 to 3 and q represents the integer 1 or 2). More preferably, this group is an oxygen atom or a group of formula —O—($CH_2$)$_p$—O— or —O—($CH_2$)$_q$—O—($CH_2$)$_q$—O— (in which p and q are as defined above).

Where E represents an alkyl group having from 1 to 6 carbon atoms, this can be a straight or branched chain group and examples include the methyl, ethyl, propyl, isopropyl, butyl, isobutyl, sec-butyl, t-butyl, pentyl, 1-ethylpropyl and hexyl groups.

Where E represents a $C_3$-$C_6$ alkenyl, $C_4$-$C_6$ alkadienyl or $C_3$ or $C_4$ alkynyl group, these likewise may be straight or branched chain groups and examples include the allyl, 1-butenyl, 2-butenyl, 1-methylallyl, 2-methylallyl, 1,3-butadienyl, 2-pentenyl, isoprenyl, 2-hexenyl, 1,4-hexadienyl, 1-propynyl, 2-propynyl and 2-butynyl groups.

Where E represents an aralkyl group having from 7 to 9 carbon atoms it may be, for example, a benzyl, phenethyl, α-methylbenzyl or α,α-dimethylbenzyl group.

Preferably E represents a $C_1$-$C_4$ alkyl group, a $C_3$ or $C_4$ alkenyl group, a propynyl group or a benzyl group.

Where $R^6$ represents a group of formula —$CH_2$—W, W may represent a group of formula —CH=N—O$R^7$, a morpholinomethyl group or a heterocyclic group.

Where $R^7$ represents a $C_1$-$C_4$ alkyl group, this may be any of the alkyl groups heretofore exemplified in relation to $R^1$.

Where $R^7$ represents an alkenyl group, this has 3 or 4 carbon atoms and is, for example, an allyl, 1-butenyl, 2-butenyl, 1-methylallyl or 2-methylallyl group, preferably an allyl group.

Where $R^7$ represents a $C_7$-$C_9$ aralkyl group, it may be, for example, a benzyl, phenethyl, 3-phenylpropyl, α-methylbenzyl or α,α-dimethylbenzyl group, preferably a benzyl group.

Where W represents a heterocyclic group, it has from 5 to 8 ring atoms, of which 2 or 3 are oxygen or sulfur hetero-atoms. It is preferably a group of formula:

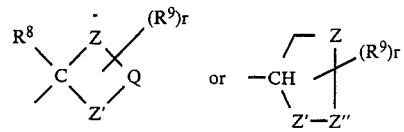

in which:

Z and Z' are independently selected from the group consisting of oxygen atoms and sulfur atoms;

Z' represents a group of formula >$CH_2$ or >S→(O)$_s$, in which s is 0, 1 or 2;

Q represents an alkylene or alkenylene group having from 2 to 5 carbon atoms, for example an ethylene, trimethylene, tetramethylene, pentamethylene, vinylene, propenylene, 1-butenylene or 2-butenylene group;

$R^8$ represents a hydrogen atom or a $C_1$-$C_4$ alkyl group, for example a methyl, ethyl, propyl or butyl group, preferably a hydrogen atom or a methyl group;

$R^9$ represents a $C_1$-$C_4$ alkyl group (e.g. as exemplified above in relation to $R^1$, and preferably a methyl, ethyl or propyl group), a $C_1$-$C_4$ haloalkyl group (e.g. a chloromethyl, bromomethyl, fluoromethyl, iodomethyl, dichloromethyl, trifluoromethyl, 2-chloroethyl, 2,2-dichloroethyl, pentabromoethyl, 3-fluoropropyl or 2,3-dibromobutyl group, preferably a halomethyl group) or a phenyl grouup; and r is 0, 1 or 2.

Examples of such heterocyclic groups include the 1,3-dioxolan-2-yl, 1,3-oxathiolan-2-yl, 1,3-dithiolan-2-yl, 1,4-dioxolan-2-yl, 1,3,2-dioxathiolan-4-yl, 1,3-dioxan-2-yl, 1,3-dioxepan-2-yl, 4,7-dihydro-1,3-dioxepin-2-yl and 1,3-dioxecan-2-yl groups. Such groups may be unsubstituted or substituted as defined above.

Preferred classes of compounds of the present invention are as follows:

(1) compounds of formula (I) and their salts, in which $R^1$ represents a hydrogen atom or a methyl group.

(2) compounds of formula (I) and their salts, in which one of $R^2$ and $R^3$ represents a methyl or ethyl group, and the other represents a methyl group, an ethyl group, a chlorine atom or a bromine atom.

(3) compounds of formula (I) and salts thereof, in which $R^2$ and $R^3$ together form a cyclopentene, cyclohexene, benzene or thiophene ring fused to the pyrimidine ring, said rings being unsubstituted or said cyclopentane, cyclohexene and benzene rings having 1 or 2 substituents selected from the group consisting of methyl, chlorine and fluoride substituents, or said thiophene ring having one or two methyl substituents.

(4) compounds of formula (I) and their salts in which $R^4$ represents a hydrogen atom, a methyl group or an ethyl group, preferably a methyl group.

(5) compounds of formula (I) and salts thereof, in which $R^5$ represents a hydrogen atom, a chlorine atom or a methyl group, preferably a hydrogen atom or a methyl group.

(6) compounds of formula (I) and salts thereof in which m is 2.

(7) compounds of formula (I) and salts thereof in which $R^6$ represents a group of formula —A—B—(DO)$_n$—E, in which A represents an alkylene group having from 1 to 5 carbon atoms, said alkylene group being unsubstituted or having a single methoxy substituent, preferably such an unsubstituted alkylene group.

(8) compounds of formula (I) and salts thereof wherein $R^6$ represents a group of formula —A—B—(DO)$_n$—E in which —B—(DO)$_n$— represents an oxygen atom, a sulfur atom, an imino group or a group of formula —NH—(CH$_2$)$_2$—O—, —O—(CH$_2$)$_p$—O— or —O—(CH$_2$)$_q$—O—(CH$_2$)$_q$—O— (in which p is an integer from 1 to 3 and q is 1 or 2), preferably said oxygen atom or group of formula —O—(CH$_2$)$_p$—or —O—(CH$_2$)$_q$—O—(CH$_2$)$_2$—O— (in which p and q are as defined above).

(9) compounds of formula (I) and salts thereof, in which $R^6$ represents a group of formula —A—B—(DO)$_n$—E, in which E represents a $C_1$-$C_4$ alkyl group, a $C_3$ or $C_4$ alkenyl group, a propynyl group or a benzyl group.

(10) compounds of formula (I) and salts thereof, in which $R^6$ represents a group of formula —CH$_2$—CH=N—OR$^7$, in which $R^7$ represents a $C_1$-$C_4$ alkyl group, an allyl group or a benzyl group.

(11) compounds of formula (I) and salts thereof, in which $R^6$ represents a group of formula —CH$_2$—W, in which W represents a group of formula

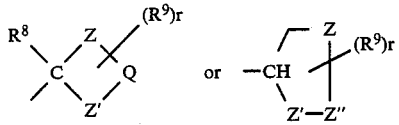

in which:
Z and Z' are independently selected from the group consisting of oxygen atoms and sulfur atoms;
Q represents an alkylene or alkenylene group having from 2 to 5 carbon atoms;
$R^8$ represents a hydrogen atom or a $C_1$-$C_4$ alkyl group;
$R^9$ represents a $C_1$-$C_4$ alkyl group, a $C_1$-$C_4$ haloalkyl group or a phenyl group;
r is 0, 1 or 2;
Z" represents a group of formula >CH$_2$ or >S→(O)$_s$; and
s is 0, 1 or 2.

(12) compounds of formula (I) and salts thereof in which :
$R^1$ represents a hydrogen atom or a methyl group;
one of $R^2$ and $R^3$ represents a methyl or ethyl group and the other represents a methyl group, an ethyl group, a chlorine atom or a bromine atom, or $R^2$ and $R^3$ together from a cyclopentene, cyclohexene, benzene or thiophene ring fused to the pyrimidine ring, said rings being unsubstituted or said cyclopentene, cyclohexene and benzene rings having one or two substituents selected from the group consisting of methyl, chlorine and fluorine substituents or said thiophene ring having one or two methyl substituents;
m is 2;
$R^4$ represents a hydrogen atom, a methyl group or an ethyl group, preferably a methyl group;
$R^5$ represents a hydrogen atom, a chlorine atom or a methyl group, preferably a hydrogen atom or a methyl group;
A represents a $C_1$-$C_5$ alkylene group or a $C_1$-$C_5$ alkylene group having a single methoxy substituent, preferably a $C_1$-$C_5$ alkylene group;
—B—(DO)$_n$— represents an oxygen atom, a sulfur atom, an imino group or a group of formula —NH—(CH$_2$)$_2$—O—, —O—(CH$_2$)$_p$—O— or —O(CH$_2$)$_q$—O—(CH$_2$)$_q$—O— (in which p is an integer from 1 to 3 and q is 1 or 2), preferably said oxygen atom or a group of formula —O—(CH$_2$)$_p$—O—, or —O—(CH$_2$)$_q$—O—(CH$_2$)$_2$—O— (in which p and q are as defined above).

(13) compounds of formula (I) and salts thereof, in which:
$R^1$ represents a hydrogen atom or a methyl group;
one of $R^2$ and $R^3$ represents a methyl or ethyl group and the other represents a chlorine atom or a bromine atom, or $R^2$ and $R^3$ form a benzene or thiophene ring fused with the pyrimidine ring;
$R^4$ represents a methyl group;
$R^5$ represents a hydrogen atom; and
$R^6$ represents a group of formula —CH$_2$—CH=N—OR$^7$, in which $R^7$ represents an ethyl group or an allyl group.

(14) compounds of formula (I) and salts thereof, in which:
$R^1$-$R^5$ are as defined in (13) above; and
$R^6$ represents a group of formula —CH$_2$—W in which W represents a group of formula

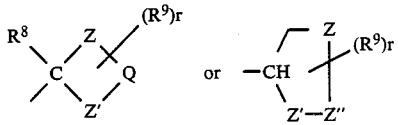

in which Z, Z', Z" and Q are as defined in (11) above, $R^8$ represents a hydrogen atom or a methyl group, $R^9$ represents a methyl group, an ethyl group or a chloromethyl group and r is 0, 1 or 2.

The compounds of the present invention contain a basic nitrogen atom and, accordingly, can readily form acid addition salts. There is no particular restriction on the nature of such salts, provided that, where the compounds are intended for agricultural or horticultural use, the resulting salts should not have a reduced activity (or unacceptably reduced activity) or increased phytotoxicity (or unacceptably increased phytotoxicity) as compared with the free base. However, where the salts are to be used for other purposes, e.g. as intermediates, even this restriction does not apply. Examples of acids which may be used to form salts include: inorganic acids, such as hydrochloric acid, hydrobromic acid, nitric acid, sulfuric acid, phosphoric acid or perchloric acid; organic carboxylic acids, such as formic acid, oxalic acid, trihaloacetic acids, fumaric acid, adipic acid, phthalic acid, malonic acid, succinic acid, glutaric acid, maleic acid and citric acid; and organic sulfonic acids, such as methanesulfonic acid, benzenesulfonic acid and p-toluenesulfonic acid.

Depending upon the various substituents, the compounds of formula (I) may exist in the form of various optical isomers and, although these isomers are indicated herein by a single formula, the present invention envisages both the individual isolated isomers and mixtures thereof. Where individual isomers are desired, these may be prepared by stereospecific synthesis techniques or a mixture of isomers may be prepared and the individual isomers separated by conventional resolution methods. As is well-known in the art, the biological activities of such isomers may differ, and it is a matter of routine experimentation to determine which of the isomers has the better activity.

Examples of compounds of the present invention are given in the following Tables 1-11, in which compounds of formula (I-1) to (I-11):

(I-1): R²R³C=C(NH-(CH₂)ₘ-O-Ar(R⁴)(R⁵)-A-O-E) with pyrimidine (R¹)

(I-2)

(I-3)

(I-4)

(I-5)

(I-6)

(I-7)

(I-8)

(I-9)

(I-10)

(I-11)

are as defined in Tables 1-11, respectively. In these Tables, the following abbreviations are used:

All—allyl
Bu—butyl
Bz—benzyl
Dit—1,3-dithiolan-2-yl
Dix—1,3-dioxolanyl
(2-Dix—1,3-dioxolan-2-yl
4-Dix—1,3-dioxolan-4-yl etc.)
Dot—1,3,2-dioxathiolan-4-yl
Et—ethyl
Mal—methallyl
Me—methyl
Mor—morpholino
Otl—1,3-oxathiolan-2-yl
Ph—phenyl
Pn—pentyl
Pr—propyl
cPr—cyclopropyl
iPr—isopropyl
Prg—propargyl (=2-propynyl)

TABLE 1

| Cpd. No. | R¹ | R² | R³ | m | R⁴ | R⁵ | A | E |
|---|---|---|---|---|---|---|---|---|
| 1 | H | Me | Cl | 2 | Me | H | —CH₂— | Me |
| 2 | H | Me | Cl | 2 | Me | H | —CH₂— | Et |
| 3 | H | Me | Cl | 2 | Me | H | —CH₂— | Pr |
| 4 | H | Me | Cl | 2 | Me | 6-Me | —CH₂— | Pr |
| 5 | H | Me | Cl | 2 | Me | H | —CH₂— | Bu |
| 6 | H | Me | Cl | 2 | Me | H | —CH₂— | Pn |
| 7 | H | Me | Cl | 2 | Me | H | —(CH₂)₂— | Me |
| 8 | H | Me | Cl | 2 | Me | 6-Me | —(CH₂)₂— | Me |
| 9 | H | Me | Cl | 2 | Me | 5-Me | —(CH₂)₂— | Me |
| 10 | H | Me | Cl | 2 | H | H | —(CH₂)₂— | Me |

TABLE 1-continued

| Cpd. No. | $R^1$ | $R^2$ | $R^3$ | m | $R^4$ | $R^5$ | A | E |
|---|---|---|---|---|---|---|---|---|
| 11 | H | Cl | Me | 2 | Me | H | $-(CH_2)_2-$ | Me |
| 12 | H | Me | Cl | 2 | Me | H | $-(CH_2)_2-$ | Et |
| 13 | H | Me | Me | 2 | Me | H | $-(CH_2)_2-$ | Et |
| 14 | H | Me | Cl | 2 | Me | 6-Me | $-(CH_2)_2-$ | Et |
| 15 | Me | Me | Cl | 2 | Me | H | $-(CH_2)_2-$ | Et |
| 16 | H | Me | Cl | 2 | Me | 3-Me | $-(CH_2)_2-$ | Et |
| 17 | H | Me | Cl | 2 | Me | 5-Me | $-(CH_2)_2-$ | Et |
| 18 | H | Me | Cl | 2 | H | H | $-(CH_2)_2-$ | Et |
| 19 | H | Me | Br | 2 | Me | H | $-(CH_2)_2-$ | Et |
| 20 | H | Me | Cl | 2 | Et | H | $-(CH_2)_2-$ | Et |
| 21 | Me | Me | Cl | 2 | Et | H | $-(CH_2)_2-$ | Et |
| 22 | H | Cl | Me | 2 | Me | H | $-(CH_2)_2-$ | Et |
| 23 | H | Br | Me | 2 | Me | H | $-(CH_2)_2-$ | Et |
| 24 | H | Cl | Me | 2 | Et | H | $-(CH_2)_2-$ | Et |
| 25 | Me | Cl | Me | 2 | Me | H | $-(CH_2)_2-$ | Et |
| 26 | H | Me | Cl | 3 | Me | H | $-(CH_2)_2-$ | Et |
| 27 | Me | Me | Cl | 3 | Me | H | $-(CH_2)_2-$ | Et |
| 28 | H | Me | Cl | 2 | Me | H | $-(CH_2)_2-$ | Pr |
| 29 | H | Cl | Me | 2 | Me | H | $-(CH_2)_2-$ | Pr |
| 30 | H | Me | Cl | 2 | Me | H | $-(CH_2)_2-$ | Bu |
| 31 | H | Me | Cl | 2 | Me | H | $-(CH_2)_2-$ | Pn |
| 32 | H | Me | Cl | 2 | Me | H | $-(CH_2)_3-$ | Me |
| 33 | H | Me | Cl | 2 | Me | H | $-(CH_2)_3-$ | Et |
| 34 | H | Me | Cl | 2 | Me | H | $-CH_2CHMe-$ | Me |
| 35 | Me | Cl | Me | 2 | Me | H | $-CH_2CHMe-$ | Me |
| 36 | H | Me | Cl | 2 | Me | H | $-CH_2CHMe-$ | Et |
| 37 | Me | Me | Cl | 2 | Me | H | $-CH_2CHMe-$ | Et |
| 38 | H | Me | Cl | 2 | Me | H | $-CH_2CHMe-$ | Pr |
| 39 | H | Me | Cl | 2 | Me | H | $-CH_2CHOMe-$ | Me |
| 40 | H | Me | Cl | 2 | Me | H | $-(CH_2)_4-$ | Me |
| 41 | H | Me | Cl | 2 | Me | H | $-(CH_2)_4-$ | Et |
| 42 | H | Me | Cl | 2 | Me | H | $-CH_2CHEt-$ | Me |
| 43 | Me | Me | Cl | 2 | Me | H | $-CH_2CHEt-$ | Et |
| 44 | H | Me | Cl | 2 | Me | H | $-CH_2CMe_2-$ | Me |
| 45 | H | Me | Me | 2 | Me | H | $-CH_2CMe_2-$ | Me |
| 46 | H | Me | Cl | 2 | Me | H | $-CH_2CH(OEt)CH_2-$ | Et |
| 47 | H | Me | Cl | 2 | Me | H | $-(CH_2)_5-$ | Me |
| 48 | H | Me | Cl | 2 | Me | H | $-(CH_2)_5-$ | Et |
| 49 | H | Me | Cl | 2 | Me | H | $-CH_2CHPr-$ | Me |
| 50 | H | Me | Cl | 2 | Me | H | $-CH_2-$ | All |
| 51 | H | Me | Cl | 2 | Me | H | $-(CH_2)_2-$ | All |
| 52 | H | Me | Cl | 2 | Me | 5-Me | $-(CH_2)_2-$ | All |
| 53 | H | Me | Cl | 2 | H | H | $-(CH_2)_2-$ | All |
| 54 | H | Cl | Me | 2 | Me | H | $-(CH_2)_2-$ | All |
| 55 | H | Me | Cl | 2 | Me | H | $-(CH_2)_2-$ | Mal |
| 56 | H | Me | Cl | 2 | Me | H | $-(CH_2)_2-$ | 3,3-diMeAll |
| 57 | H | Me | Cl | 2 | Me | H | $-CH_2CHMe-$ | All |
| 58 | Me | Me | Cl | 2 | Me | H | $-CH_2CHMe-$ | All |
| 59 | H | Me | Cl | 2 | Me | H | $-CH_2-$ | Prg |
| 60 | H | Me | Cl | 2 | Me | H | $-(CH_2)_2-$ | Prg |
| 61 | Me | Me | Cl | 2 | Me | H | $-(CH_2)_2-$ | Prg |
| 62 | H | Cl | Me | 2 | Me | H | $-(CH_2)_2-$ | Prg |
| 63 | H | Me | Cl | 2 | Me | H | $-(CH_2)_2-$ | Bz |
| 64 | Me | Me | Cl | 2 | Me | H | $-(CH_2)_2-$ | Bz |
| 65 | H | Me | Cl | 2 | Me | 5-Me | $-(CH_2)_2-$ | Bz |
| 66 | H | Me | Br | 2 | Me | H | $-(CH_2)_2-$ | Bz |
| 67 | H | Cl | Me | 2 | Me | H | $-(CH_2)_2-$ | Bz |
| 68 | Me | Cl | Me | 2 | Me | 6-Me | $-(CH_2)_2-$ | Bz |
| 69 | H | Me | Cl | 2 | Me | H | $-CH_2CHMe-$ | Bz |
| 70 | Me | Me | Cl | 2 | Me | H | $-CH_2CHMe-$ | Bz |
| 71 | H | Cl | Et | 2 | Me | H | $-(CH_2)_2-$ | Et |
| 72 | H | Pr | Cl | 2 | Me | H | $-(CH_2)_2-$ | Et |
| 73 | H | Cl | Cl | 2 | Me | H | $-(CH_2)_2-$ | Et |
| 74 | H | Et | Cl | 2 | Me | H | $-(CH_2)_2-$ | Et |
| 75 | H | Et | Cl | 2 | Me | 3-Me | $-(CH_2)_2-$ | Et |
| 76 | H | Pr | Cl | 2 | Me | 3-Me | $-(CH_2)_2-$ | Et |
| 77 | H | Et | Cl | 2 | Me | H | $-(CH_2)_2-$ | Bz |
| 78 | H | Et | Cl | 2 | Me | H | $-(CH_2)_2-$ | Me |
| 79 | H | Et | Cl | 2 | Me | H | $-(CH_2)_2-$ | Pr |
| 80 | H | Et | Cl | 2 | Me | H | $-(CH_2)_2-$ | Bu |
| 81 | H | Et | Cl | 2 | Me | H | $-(CH_2)_2-$ | All |
| 82 | H | iPr | Cl | 2 | Me | H | $-(CH_2)_2-$ | Et |
| 83 | H | iPr | Cl | 2 | Me | 3-Me | $-(CH_2)_2-$ | Et |
| 84 | H | iPr | Cl | 2 | Me | H | $-(CH_2)_2-$ | Bz |
| 85 | H | cPr | Cl | 2 | Me | H | $-(CH_2)_2-$ | Et |
| 86 | H | Me | Cl | 2 | Me | 3-Me | $-(CH_2)_2-$ | Me |
| 87 | H | Me | Cl | 2 | Me | 3-Me | $-(CH_2)_2-$ | All |
| 88 | H | Et | Cl | 2 | Me | 3-Me | $-(CH_2)_2-$ | Me |
| 89 | H | Et | Cl | 2 | Me | 3-Me | $-(CH_2)_2-$ | Pr |
| 80 | H | Et | Cl | 2 | Me | 3-Me | $-(CH_2)_2-$ | All |

TABLE 1-continued

| Cpd. No. | R¹ | R² | R³ | m | R⁴ | R⁵ | A | E |
|---|---|---|---|---|---|---|---|---|
| 91 | H | Et | Me | 2 | Me | H | —(CH$_2$)$_2$— | Et |
| 92 | H | Et | Me | 2 | Me | 3-Me | —(CH$_2$)$_2$— | Et |
| 93 | H | Et | Me | 2 | Me | H | —(CH$_2$)$_2$— | Bz |
| 94 | H | Et | Et | 2 | Me | H | —(CH$_2$)$_2$— | Et |
| 95 | H | Et | Et | 2 | Me | 3-Me | —(CH$_2$)$_2$— | Et |
| 96 | H | Et | Et | 2 | Me | H | —(CH$_2$)$_2$— | Bz |
| 97 | Me | Et | Cl | 2 | Me | H | —(CH$_2$)$_2$— | Et |
| 98 | Me | Et | Cl | 2 | Me | 3-Me | —(CH$_2$)$_2$— | Et |
| 99 | H | Et | Br | 2 | Me | H | —(CH$_2$)$_2$— | Et |
| 100 | H | Et | Br | 2 | Me | H | —(CH$_2$)$_2$— | Bz |
| 101 | H | Et | Br | 2 | Me | 3-Me | —(CH$_2$)$_2$— | Et |
| 102 | Cl | Et | Cl | 2 | Me | H | —(CH$_2$)$_2$— | Et |
| 103 | Me | MeSCH$_2$ | Cl | 2 | Me | H | —(CH$_2$)$_2$— | Et |
| 104 | Me | MeOCH$_2$ | Cl | 2 | Me | H | —(CH$_2$)$_2$— | Et |
| 105 | H | MeOCH$_2$ | Cl | 2 | Me | H | —(CH$_2$)$_2$— | Et |
| 106 | H | MeSCH$_2$ | Cl | 2 | Me | H | —(CH$_2$)$_2$— | Et |

TABLE 2

| Cpd No | R² | R³ | A | B' | E |
|---|---|---|---|---|---|
| 107 | Me | Cl | —CH$_2$— | —S— | Et |
| 108 | Me | Cl | —CH$_2$— | —S— | Pr |
| 109 | Me | Cl | —(CH$_2$)$_2$— | —S— | Et |
| 110 | Me | Cl | —(CH$_2$)$_2$— | —S— | Bz |
| 111 | Me | Cl | —(CH$_2$)$_2$— | —NH— | Et |
| 112 | Me | Cl | —(CH$_2$)$_2$— | —NH(CH$_2$)$_2$O— | Et |
| 113 | Me | Cl | —CH$_2$— | —O(CH$_2$)$_2$O— | Et |
| 114 | Me | Cl | —CH$_2$— | —O(CH$_2$)$_2$O— | iPr |
| 115 | Me | Cl | —(CH$_2$)$_2$— | —OCH$_2$O— | Me |
| 116 | Cl | Me | —(CH$_2$)$_2$— | —OCH$_2$O— | Me |
| 117 | Me | Cl | —(CH$_2$)$_2$— | —O(CH$_2$)$_2$O— | Me |
| 118 | Me | Cl | —(CH$_2$)$_2$— | —O(CH$_2$)$_2$O— | Et |
| 119 | Cl | Me | —(CH$_2$)$_2$— | —O(CH$_2$)$_2$O— | Et |
| 120 | Me | Cl | —(CH$_2$)$_2$— | —O(CH$_2$)$_2$O— | iPr |
| 121 | Me | Cl | —(CH$_2$)$_2$— | —O(CH$_2$)$_2$O— | Bu |
| 122 | Me | Cl | —(CH$_2$)$_2$— | —O(CH$_2$)$_2$O— | All |
| 123 | Me | Cl | —(CH$_2$)$_2$— | —O(CH$_2$)$_2$O— | Bz |
| 124 | Me | Cl | —(CH$_2$)$_2$— | —O(CH$_2$)$_3$O— | Et |
| 125 | Cl | Me | —(CH$_2$)$_2$— | —O(CH$_2$)$_3$O— | Et |
| 126 | Me | Cl | —CH$_2$— | —O(CH$_2$)$_2$O(CH$_2$)$_2$O— | Et |
| 127 | Me | Cl | —(CH$_2$)$_2$— | —OCH$_2$O(CH$_2$)$_2$O— | Me |
| 128 | Me | Cl | —(CH$_2$)$_2$— | —O(CH$_2$)$_2$O(CH$_2$)$_2$O— | Me |
| 129 | Me | Cl | —(CH$_2$)$_2$— | —O(CH$_2$)$_2$O(CH$_2$)$_2$O— | Et |
| 130 | Me | Cl | —(CH$_2$)$_2$— | —O(CH$_2$)$_2$O(CH$_2$)$_2$O— | Bu |

TABLE 3

| Cpd No | R¹ | R² | R³ | R⁵ | B' |
|---|---|---|---|---|---|
| 131 | Me | Cl | Me | H | —O(CH$_2$)$_3$O— |
| 132 | H | Me | Cl | 3-Cl | —O— |
| 133 | H | Me | Cl | 6-Cl | —O— |

TABLE 4

| Cpd. No. | R$^{2a}$ | R$^{3a}$ | m | R⁴ | R⁵ | A | E |
|---|---|---|---|---|---|---|---|
| 134 | H | H | 2 | Me | H | —(CH$_2$)$_2$— | Me |
| 135 | H | H | 2 | Me | H | —(CH$_2$)$_2$— | Pr |
| 136 | H | H | 2 | Me | H | —(CH$_2$)$_2$— | Bu |
| 137 | H | H | 2 | Me | H | —(CH$_2$)$_2$— | Et |
| 138 | H | H | 2 | Me | 5-Me | —(CH$_2$)$_2$— | Et |
| 139 | H | H | 2 | Et | H | —(CH$_2$)$_2$— | Et |
| 140 | H | H | 2 | Cl | H | —(CH$_2$)$_2$— | Et |
| 141 | H | H | 2 | Me | H | —(CH$_2$)$_2$— | All |
| 142 | H | H | 2 | Me | H | —(CH$_2$)$_2$— | Bz |
| 143 | H | H | 2 | Me | H | —(CH$_2$)$_3$— | Et |
| 144 | H | H | 2 | Me | H | —CH$_2$CHMe— | Et |
| 145 | H | H | 2 | Me | H | —(CH$_2$)$_4$— | Me |
| 146 | H | Me | 2 | Me | H | —(CH$_2$)$_2$— | Et |
| 147 | H | Me | 3 | Me | H | —(CH$_2$)$_2$— | Et |
| 148 | H | Me | 2 | Me | H | —(CH$_2$)$_2$— | Bz |
| 149 | Me | Me | 2 | Me | H | —(CH$_2$)$_2$— | Et |
| 150 | H | H | 2 | Me | H | —CH$_2$CHEt— | Me |

TABLE 4-continued

| Cpd. No. | R$^{2a}$ | R$^{3a}$ | m | R⁴ | R⁵ | A | E |
|---|---|---|---|---|---|---|---|
| 151 | H | H | 2 | Me | H | —CH$_2$CHEt— | Et |
| 152 | H | H | 2 | Me | 6-Cl | —(CH$_2$)$_2$— | Et |
| 153 | H | H | 2 | Me | 3-Me | —(CH$_2$)$_2$— | Et |

TABLE 5

| Cpd No. | R² + R³ | A | E |
|---|---|---|---|
| 154 | —(CH$_2$)$_3$— | —(CH$_2$)$_2$— | Et |
| 155 | —(CH$_2$)$_3$— | —(CH$_2$)$_2$— | All |
| 156 | —(CH$_2$)$_3$— | —CH$_2$CHMe— | Bz |
| 157 | —(CH$_2$)$_4$— | —(CH$_2$)$_2$— | Et |
| 158 | —(CH$_2$)$_4$— | —CH$_2$CHMe— | Bz |
| 159 | —CH$_2$CH=CHCH$_2$— | —(CH$_2$)$_2$— | Et |

TABLE 6

| Cpd. No. | R$^{2b}$ | R$^{3b}$ | m | R⁴ | R⁵ | A | E |
|---|---|---|---|---|---|---|---|
| 160 | H | H | 2 | Me | H | —(CH$_2$)$_2$— | Me |
| 161 | H | H | 2 | Me | 5-Me | —(CH$_2$)$_2$— | Me |
| 162 | H | H | 2 | Me | 6-Me | —(CH$_2$)$_2$— | Me |
| 163 | H | H | 3 | Me | H | —(CH$_2$)$_2$— | Me |
| 164 | H | H | 2 | Me | H | —(CH$_2$)$_2$— | Et |
| 165 | H | H | 2 | Me | 5-Me | —(CH$_2$)$_2$— | Et |
| 166 | H | H | 2 | H | H | —(CH$_2$)$_2$— | Et |
| 167 | H | H | 2 | Et | H | —(CH$_2$)$_2$— | Et |
| 168 | H | H | 2 | Cl | H | —(CH$_2$)$_2$— | Et |
| 169 | H | H | 2 | Me | H | —CH$_2$CHMe— | Me |
| 170 | H | H | 2 | Me | H | —(CH$_2$)$_4$— | Me |
| 171 | H | H | 2 | Me | H | —CH$_2$CHEt— | Me |
| 172 | H | H | 2 | Me | H | —CH$_2$CHEt— | Et |
| 173 | H | H | 2 | Me | H | —CH$_2$CMe$_2$— | Me |
| 174 | H | H | 2 | Me | H | —(CH$_2$)$_2$— | All |
| 175 | H | H | 2 | Me | 5-Me | —(CH$_2$)$_2$— | All |
| 176 | H | H | 2 | Me | H | —(CH$_2$)$_2$— | Prg |
| 177 | H | H | 2 | Me | H | —(CH$_2$)$_2$— | Bz |
| 178 | H | H | 2 | Me | 5-Me | —(CH$_2$)$_2$— | Bz |
| 179 | H | H | 2 | Me | H | —CH$_2$CHMe— | Bz |
| 180 | H | Me | 2 | Me | H | —(CH$_2$)$_2$— | Et |
| 181 | H | F | 2 | Me | H | —(CH$_2$)$_2$— | Et |
| 182 | H | F | 3 | Me | H | —(CH$_2$)$_2$— | Et |
| 183 | H | F | 2 | Me | H | —CH$_2$CHMe— | Bz |
| 184 | Cl | H | 2 | Me | H | —(CH$_2$)$_2$— | Et |
| 185 | H | H | 2 | Me | 6-Cl | —(CH$_2$)$_2$— | Et |

TABLE 7

| Cpd. No. | R² | R³ | R⁵ | A | E |
|---|---|---|---|---|---|
| 186 | Me | Cl | H | —(CH$_2$)$_4$— | All |
| 187 | Cl | Me | 6-Cl | —(CH$_2$)$_2$— | Et |
| 188 | Me | Me | 6-Cl | —(CH$_2$)$_2$— | Et |

TABLE 7-continued

| Cpd. No. | R² | R³ | R⁵ | A | E |
|---|---|---|---|---|---|
| 189 | Me | Cl | 5-Cl | —(CH₂)₂— | Et |

TABLE 8

| Cpd. No. | R¹ | R² | R³ | W |
|---|---|---|---|---|
| 190 | H | Me | Cl | —CH═NOMe |
| 191 | H | Me | Cl | —CH═NOEt |
| 192 | H | Me | Br | —CH═NOEt |
| 193 | Me | Me | Cl | —CH═NOEt |
| 194 | H | Cl | Me | —CH═NOEt |
| 195 | H | Me | Cl | —CH═NOPr |
| 196 | H | Me | Cl | —CH═NOAll |
| 197 | H | Me | Cl | —CH═NOBz |
| 198 | H | Me | Cl | —CH₂Mor |
| 199 | H | Me | Cl | 2-Dix |
| 200 | H | Cl | Me | 2-Dix |
| 201 | H | Me | Cl | 2-Me—2-Dix |
| 202 | H | Me | Cl | 4-Me—2-Dix |
| 203 | H | Me | Cl | 4-Et—2-Dix |
| 204 | H | Me | Cl | 4-Pr—2-Dix |
| 205 | H | Me | Cl | 4-(ClCH₂)—2-Dix |
| 206 | H | Me | Cl | 4,5-DiMe—2-Dix |
| 207 | H | Me | Br | 2-Dix |
| 208 | Me | Me | Cl | 2-Dix |
| 209 | H | Me | Cl | Otl |
| 210 | H | Me | Cl | Dit |
| 211 | H | Me | Cl | 2,2-diMe—4-Dix |
| 212 | H | Cl | Me | 2,2-diMe—4-Dix |
| 213 | H | Me | Cl | 2-Et—2-Me—4-Dix |
| 214 | H | Me | Cl | 2,2-diEt—4-Dix |
| 215 | H | Me | Cl | 2-Ph—4-Dix |
| 216 | H | Me | Cl | 2-(O═)-Dot |
| 217 | H | Me | Cl | 1,3-dioxan-2-yl |
| 218 | H | Cl | Me | 1,3-dioxan-2-yl |
| 219 | H | Me | Cl | 2-Me-1,3-dioxan-2-yl |
| 220 | H | Me | Cl | 4-Me-1,3-dioxan-2-yl |
| 221 | H | Me | Cl | 5,5-diMe-1,3-dioxan-2-yl |
| 222 | H | Me | I | 2-Me-1,3-dioxepan-2-yl |
| 223 | H | Me | Cl | 1,3-dioxepan-2-yl |
| 244 | H | Cl | Me | 1,3-dioxepan-2-yl |
| 225 | H | Me | Br | 1,3-dioxepan-2-yl |
| 226 | Me | Me | Cl | 1,3-dioxepan-2-yl |
| 227 | H | Me | Cl | 1,3-dioxocan-2-yl |
| 228 | H | Me | Cl | 4,7-dihydro-1,3-dioxepin-2-yl |

TABLE 9

| Cpd No. | Py | W |
|---|---|---|
| 229 | benzo[d]pyrimidin-4-yl | 2-Dix |
| 230 | thieno[2,3-d]Pyrimidin-4-yl | 2-Dix |
| 231 | benzo[d]Pyrimidin-4-yl | 2,2-diMe—4-Dix |
| 232 | thieno[2,3-d]pyrimidin-4-yl | 1,3-dioxepan-2-yl |
| 233 | thieno[2,3-d]pyrimidin-4-yl | —CH═NOEt |

TABLE 10

| Cpd. No. | R²ᶜ | R³ᶜ | R⁵ | E |
|---|---|---|---|---|
| 234 | Me | Me | H | Et |
| 235 | Me | H | H | Et |
| 236 | H | Me | H | Et |
| 237 | H | Me | H | Bz |
| 238 | H | Me | H | Me |
| 239 | H | Me | H | Pr |
| 240 | H | Me | H | Bu |
| 241 | H | Me | H | All |
| 242 | H | Me | H | Prg |
| 243 | H | Me | 3-Me | Et |

TABLE 11

TABLE 11-continued

| Cpd. No. | R⁵ | E |
|---|---|---|
| 244 | H | Et |
| 245 | H | Bz |
| 246 | H | Me |
| 247 | H | Pr |
| 248 | H | All |
| 249 | H | Prg |
| 250 | 3-Me | Et |

Compound No. 251

Formula (I) in which R¹ = H, R² = Et, R³ = Cl, m = 2, R⁴ = Me, R⁵ = 3-Me, A = —(CH₂)₂—, —B—(DO)ₙ— = —O—, E = Bz.

Of the compounds listed above, preferred compounds are Compounds No. 12, 75 and 99 and their acid addition salts.

Compounds of the invention can be prepared by the methods illustrated below.

METHOD A

The compounds of the invention may be prepared by condensation between a pyrimidine derivative of formula (II) and a phenoxyalkylamine of formula (III), as illustrated in the following reaction scheme:

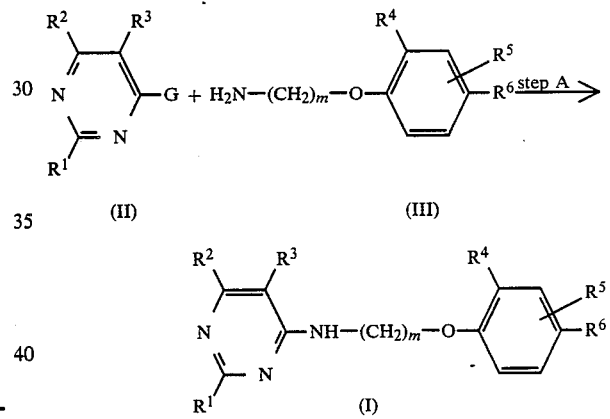

In the above formulae, R¹, R², R³, R⁴, R⁵, R⁶ and m are as defined above. G represents a radical to be eliminated. Amine condensation reactions of this type are well-known and the radical G may be any radical known for use in this type of reaction, without any particular limitation. Non-limiting examples of radicals which may be employed include: halogen atoms, such as chlorine, bromine or iodine atoms; C₁-C₄ alkylthio groups, such as the methylthio, ethylthio, propylthio or butylthio groups; C₁-C₄ alkanesulfonyloxy groups, in which the alkyl part is unsubstituted or has one or more halogen substituents, such as the methanesulfonyloxy, ethanesulfonyloxy or trifluoromethanesulfonyloxy groups; arenesulfonyloxy groups, such as the benzenesulfonyloxy or p-toluenesulfonyloxy groups; and the hydroxy group.

As can be seen clearly from the above reaction scheme, a compound of formula H-G is eliminated in the course of this reaction and it is, therefore, preferred to carry out the reaction in the presence of a scavenging compound which removes the compound H-G from the reaction mixture and thus facilitates the reaction; where the compound H-G is an acid, the scavenging compound is preferably an acid-binding agent and thus most preferably a base.

There is no particular restriction on the nature of the base to be employed, and examples of suitable bases include: organic bases, such as triethylamine, pyridine or N,N-diethylaniline; alkali metal hydroxides, such as sodium hydroxide or potassium hydroxide; and alkali metal carbonates, such as sodium carbonate or potassium carbonate.

The reaction is usually conducted in the presence of a solvent; however, it will also take place if the compounds of formulae (II) and (III) are heated to fusion in the absence of a solvent. Where a solvent is employed, its nature is not critical, provided that it has no adverse effect upon the reaction. Examples of suitable solvents include: aromatic, aliphatic and cycloaliphatic hydrocarbons and halogenated (e.g. chlorinated) derivatives thereof, such as benzene, toluene, xylene, methylnaphthalene, petroleum, ether, ligroin, hexane, chlorobenzene, dichlorobenzene, methylene chloride, chloroform, 1,2-dichloroethane, trichloroethylene or cyclohexane; ethers, such as diethyl ether, ethylene glycol dimethyl ether, tetrahydrofuran or dioxane; ketones, such as acetone or methyl ethyl ketone; alcohols, such as methanol, ethanol or ethylene glycol, and mixtures of such alcohols with water; and mixtures of any two or more of the above solvents.

The reaction will take place over a wide range of temperatures and the precise reaction temperature chosen is not particularly critical. Usually, we prefer to carry out the reaction at a temperature which is not below room temperature and not greater than the boiling point of the solvent (if a solvent is employed) or not greater than the fusion temperature of the two reagents (if no solvent is employed). Preferably, in order to reduce the reaction time, the reaction is carried out with heating.

METHOD B

Compounds of the invention in which $R^6$ represents a group of formula —A—B—(DO)$_n$—E, that is to say compounds of formula (VI), may be prepared by the reaction illustrated in the following reaction scheme:

In the above formulae, $R^1$, $R^2$, $R^3$, $R^4$, $R^5$, G, m, A, B, D and n are as defined above. X represents a halogen atom.

Step B1

In this step, a compound of formula (II) is condensed with a substituted phenoxyalkylamine of formula (IV). The reaction involved is essentially the same as that involved in Method A, described above, and may be carried out under the same conditions and employing the same solvents as described in relation to Method A.

Step B2

In this step, the compound of formula (V), prepared in step B1, is first reacted with a base and then reacted with a halogen compound of formula E—(OD)$_n$—X, to give the desired compound of formula (VI).

The nature of the base employed in the first part of this step is not critical, although we generally prefer to employ an inorganic base. Examples include: alkali metals, such as potassium or sodium; alkali metal hydrides, such as sodium hydride or potassium hydride; alkali metal amides, such as sodium amide; and alkali metal carbonates, such as sodium carbonate or potassium carbonate.

In the second part of this step, the resulting compound is reacted with the compound of formula E—(OD)$_n$—X. X represents a halogen atom and is preferably a chlorine or bromine atom.

Both parts of this step are preferably carried out in the presence of a solvent, the nature of which is not critical, provided that it has no adverse effect upon the reaction. Examples of suitable solvents include: ethers, such as diethyl ether, ethylene glycol dimethyl ether or dioxane; ketones, such as acetone or methyl ethyl ketone; and dimethylformamide.

The reaction will take place over a wide range of temperatures and the precise temperature chosen is not critical. However, in order to speed the reaction, we generally prefer that it should be carried out at a temperature greater than room temperature, and up to the

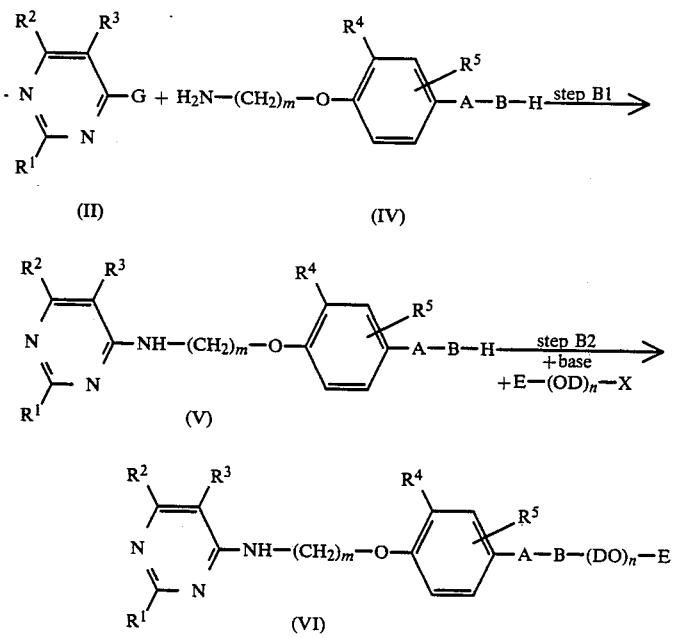

boiling point of the solvent. Generally, the reaction is carried out with heating.

METHOD C

Compounds of the invention in which B represents a sulfur atom or an imino group, that is to say compounds of formula (XII), may be prepared as illustrated in the following reaction scheme:

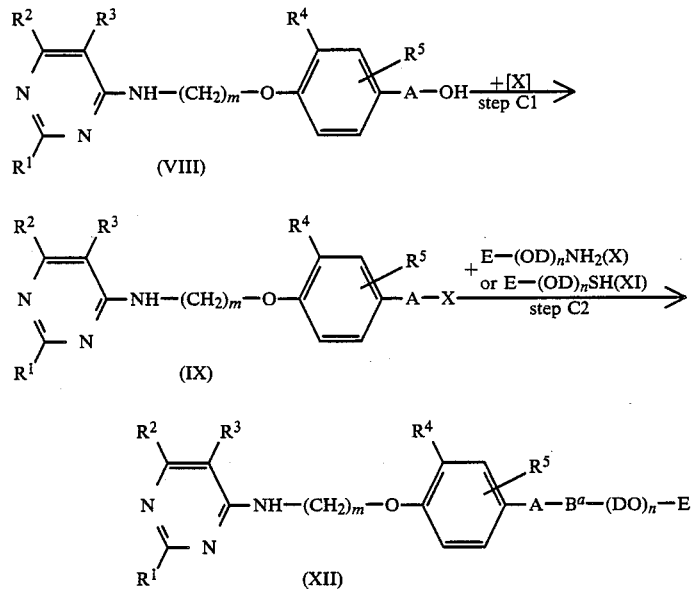

In the above formulae, $R^1$, $R^2$, $R^3$, $R^4$, $R^5$, m, A, X, E, D and n are as defined above. [X] represents a halogenating agent. $B^a$ represents a sulfur atom or an imino group. The starting material for this reaction scheme, the compound of formula (VIII), may be prepared following essentially the same procedure as described in Method A.

Step C1

In this step, the compound of formula (VIII) is reacted with a halogenating agent [X]. The nature of the halogenating agent employed is not critical and any halogenating agent commonly used in organic reactions may equally be used here, provided that it has no adverse effect upon the remainder of the molecule. Suitable halogenating agents include, for example: thionyl halides, such as thionyl chloride or thionyl bromide; phosphorus oxyhalides, such as phosphorus oxychloride or phosphorus oxybromide; phosphorus pentahalides, such as phosphorus pentachloride; and phosphorus trihalides, such as phosphorus trichloride or phosphorus tribromide.

The reaction is preferably effected in the presence of a solvent, the nature of which is not critical, provided that it has no adverse effect upon the reaction. Suitable solvents include, for example: aromatic, aliphatic and cycloaliphatic hydrocarbons, which may be halogenated, such as benzene, toluene, xylene, methylnaphthalene, petroleum ether, ligroin, hexane, chlorobenzene, methylene chloride, chloroform, trichloroethylene or cyclohexane; and ethers, such as diethyl ether, ethylene glycol dimethyl ether, tetrahydrofuran or dioxane. The reaction is preferably effected in the presence of a base, which likewise is not critical, although we generally prefer an organic base, such as triethylamine, pyridine or N,N-diethylaniline.

The reaction will take place over a wide range of temperatures and the precise temperature chosen is not critical. However, we generally prefer to carry out the reaction at a temperature between room temperature and the boiling point of the solvent employed, preferably with heating.

Step C2

In this step, the compound of formula (IX), prepared as in step C1, is reacted with an amine (X) or a mercaptan (XI), to give the desired compound of formula (XII).

The reaction is preferably effected in the presence of a solvent, the nature of which is not critical, provided that it has no adverse effect upon the reaction. Suitable solvents include, for example: aromatic, aliphatic and cycloaliphatic hydrocarbons, which may be halogenated, such as benzene, toluene, xylene, methylnaphthalene, petroleum ether, ligroin, hexane, chlorobenzene, methylene chloride, chloroform, trichloroethylene or cyclohexane; ethers, such as diethyl ether, ethylene glycol dimethyl ether, tetrahydrofuran or dioxane; and alcohols, such as methanol, ethanol or ethylene glycol.

The reaction will take place over a wide range of temperatures, and we generally prefer to carry out the reaction at a temperature within the range from room temperature to 150° C., more preferably with heating. Particularly where the amine (X) is employed, the reaction is preferably effected under superatmospheric pressure, in order to allow a higher temperature to be used.

METHOD D

Compounds of the invention in which $R^2$ and $R^3$ together form an optionally substituted furan or thiophene ring, e.g. compounds of formula (XV), can be prepared as illustrated in the following reaction scheme:

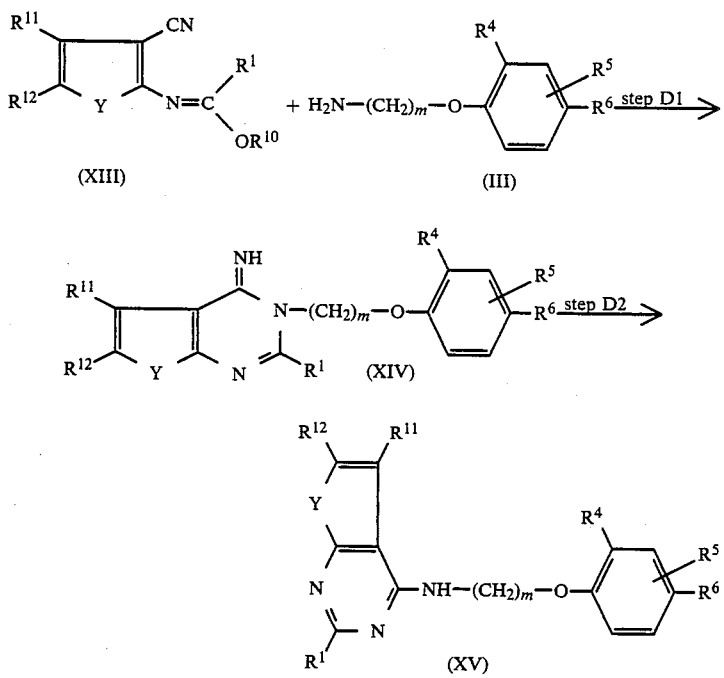

In the above formulae, $R^1$, $R^4$, $R^5$, $R^6$ and m are as defined above. Y represents an oxygen or sulfur atom. $R^{11}$ and $R^{12}$ are optional substituents on the furan or thiophene ring, that is to say they may be the same or different and each represents a hydrogen atom, a $C_1$-$C_4$ alkyl group or a halogen atom. $R^{10}$ represents a $C_1$-$C_4$ alkyl group, e.g. as defined above in relation to $R^1$.

Step D1

In this step, the 3-cyano-2-(alkoxymethylene)iminothiophene (or furan) of formula (XIII) is reacted with a substituted phenoxyalkylamine of formula (III), as described in J. Org. Chem., 32, 2376 (1967) or Bull. Soc. Chem. Fr., (1975), 592. Examples of solvents, which are not critical, are the same as those employed in step C2 of Method C, especially the alcohols.

Compounds of the invention in which the thienopyrimidine or furopyrimidine part of the compound of formula (XV) has the partial formula (If) or (Ih) can be prepared by a corresponding reaction starting with a compound of formula (XVI), in place of the compound of formula (XIII):

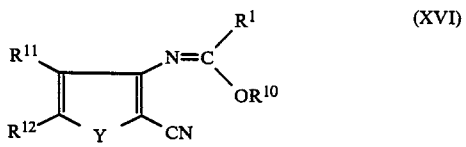

Step D2

The resulting compound of formula (XIV), with or without isolation from the reaction mixture, is then treated with a base, to catalyse its rearrangement to the desired compound of formula (XV).

There is no particular restriction on the nature of the base employed, provided that it does not have any adverse effect on other parts of the molecule. Suitable bases include: alkali metals, such as sodium or potassium; and alkali metal alkoxides, such as sodium methoxide or sodium ethoxide.

The reaction will take place over a wide range of temperatures, although we generally prefer to carry it out with heating, in order to accelerate it. In general, a reaction temperature between room temperature and the reflux temperature of the solvent is preferred.

METHOD E

Compounds of the invention in which $R^6$ represents a group of formula —$CH_2$—W and W represents a group of formula

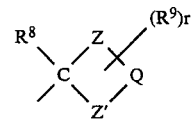

that is to say compounds of formula (XIX), can be prepred as illustrated in the following reaction scheme:

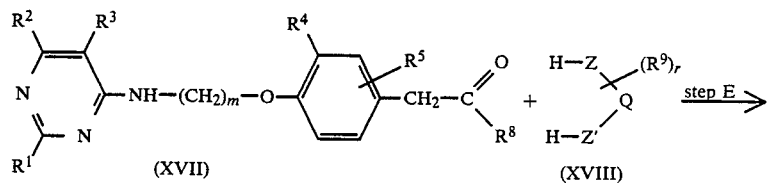

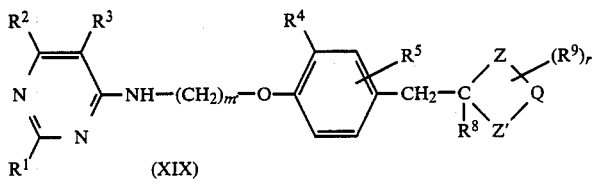

(XIX)

In the above formulae, $R^1$, $R^2$, $R^3$, $R^4$, $R^5$, $R^8$, $R^9$, m, r, Z, Z' and Q are as defined above.

This reaction consists of reacting the compound of formula (XVII) (which may have been prepared following the procedures described in Method A) with a diol, dithiol or thioalcohol of formula (XVIII) in the presence of an acid catalyst. There is no particular limitation on the nature of the acid catalyst employed and any acid which does not react with either of the two reagents may be employed. Examples include: alkanesulfonic acids in which the alkane part may be unsubstituted or have one or more halogen substituents, such as methanesulfonic acid, ethanesulfonic acid or trifluoromethanesulfonic acid; arenesulfonic acids, such as benzenesulfonic acid or p-toluenesulfonic acid; and mineral acids, such as sulfuric acid or hydrochloric acid.

The reaction is preferably effected in the presence of a solvent, the nature of which is not critical, provided that it has no adverse effect upon the reaction. Examples of suitable solvents include aromatic, aliphatic and cycloaliphatic hydrocarbons, which may or may not be halogenated (e.g. chlorinated), such as benzene, toluene, xylene, methylnaphthalene, chlorobenzene, dichlorobenzene, methylene chloride, chloroform, 1,2-dichloroethane, trichloroethylene or cyclohexane.

The reaction will take place over a wide range of temperatures and the precise reaction temperature chosen is not particularly critical. In general, however, we prefer to carry out the reaction at a temperature not less than room temperature and not more than the boiling temperature of the solvent employed. However, as is apparent from the reaction illustrated above, water is eliminated in this reaction and it is, therefore, preferred to carry out the reaction at the azeotropic point of water and the solvent, in order to remove water from the reaction system and thereby facilitate the reaction.

METHOD F

Compounds of the invention in which $R^6$ represents a group of formula —$CH_2$—W and W represents a group of formula

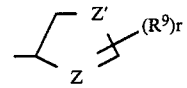

that is to say compounds of formula (XXII), may be prepared by reacting a compound of formula (XX) with a ketone or aldehyde of formula (XXI) in the presence of an acid catalyst, as illustrated in the following reaction scheme:

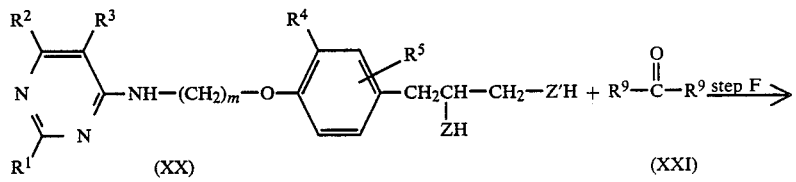

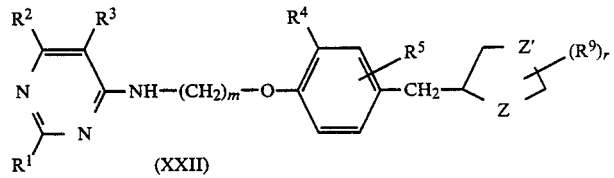

(XXII)

In the above formulae, $R^1$, $R^2$, $R^3$, $R^4$, $R^5$, $R^9$, m, r, Z and Z' are as defined above.

The reaction is similar to that described above in Method E and may be carried out employing the same acid catalysts, solvents and reaction temperatures.

METHOD G

Compounds of the invention in which $R^6$ represents a group of formula —$CH_2$—W and W represents a group of formula

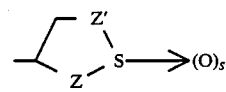

that is to say compounds of formula (XXIV), may be prepared as illustrated in the following reaction scheme:

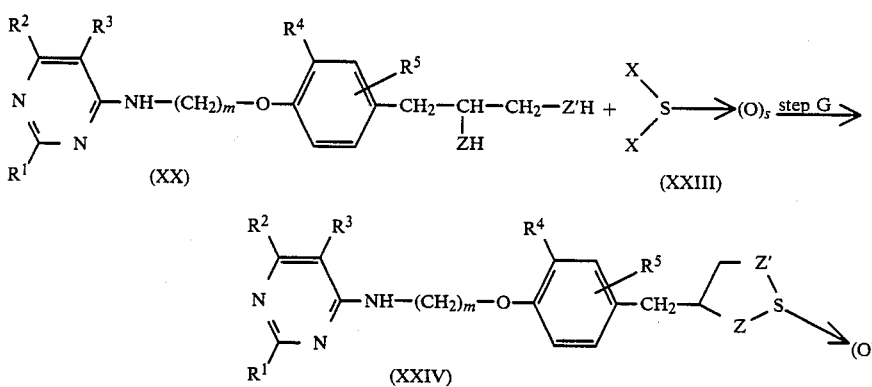

In the above formulae $R^1$, $R^2$, $R^3$, $R^4$, $R^5$, m, Z, Z', X and s are as defined above.

The reaction is effected by reacting the compound of formula (XX) with a thionyl halide, sulfinyl halide or sulfonyl halide of formula (XXIII) in the presence of an organic base.

There is no particular restriction on the nature of the organic base to be employed, since its principal function is to react with and eliminate from the reaction system the hydrogen halide generated by the reaction. Suitable organic bases include pyridine, triethylamine and N,N-dimethylaniline.

The reaction is preferably effected in the presence of a solvent, the nature of which is not critical, provided that it has no adverse effect on the reaction. Suitable solvents include, for example: aromatic, aliphatic and cycloaliphatic hydrocarbons, which may or may not be halogenated (e.g. chlorinated), such as benzene, toluene, xylene, methylnaphthalene, petroleum ether, ligroin, hexane, chlorobenzene, methylene chloride, chloroform, 1,2-dichloroethane, trichloroethylene and cyclohexane; and ethers such as diethyl ether, ethylene glycol dimethyl ether, tetrahydrofuran and dioxane.

The reaction will take place over a wide range of temperatures, and the precise temperature chosen is not particularly critical to the reaction. Generally, we will carry out the reaction at a temperature or temperatures within the range from 0° C. to the boiling point of the solvent employed. Most preferably, the reaction mixture is cooled whilst the thionyl, sulfinyl or sulfonyl halide (XXIII) is added dropwise, and then, when the dropwise addition is complete, the reaction mixture is heated.

METHOD H

Compounds of the invention in which $R^6$ represents a group of formula $-CH_2-W$ and W represents a group of formula $-CH=NOR^7$, that is to say compounds of formula (XXVI) ($R^7=H$) or (XXVII), can be prepared as illustrated in the following reaction scheme:

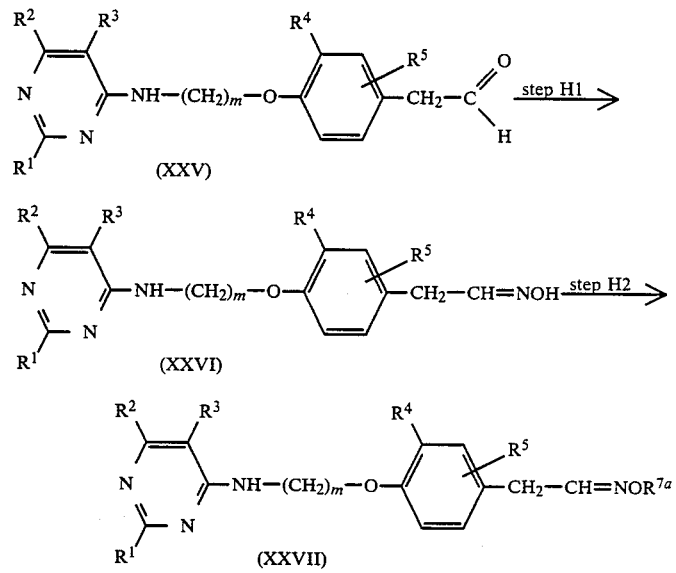

In the above formulae, $R^1$, $R^2$, $R^3$, $R^4$, $R^5$ and m are as defined above. $R^{7a}$ represents any of the groups represented by $R^7$ but not a hydrogen atom.

Step H1

The first step in this reaction involves reacting the compound of formula (XXV) (which may have been prepared by a procedure similar to that described in Method A) with a hydroxylamine salt, for example hyroxylamine hydrochloride or hydroxylamine sulfate, to give the compound of formula (XXVI).

The reaction is preferably effected in the presence of a solvent, the nature of which is not critical, provided that it has not adverse effect upon the reaction. The solvent is preferably water-miscible, and examples of suitable solvents include: alcohols, such as methanol or ethanol; and ethers, such as dioxane or tetrahydrofuran. The alcohols are preferred.

The reaction is preferably effected in the presence of a base, preferably an inorganic base, such as an alkali metal hydroxide (e.g. sodium or potassium hydroxide) or an alkali metal carbonate (e.g. sodium or potassium carbonate), of which the hydroxides are preferred.

The reaction will take place over a wide range of temperatures and the precise temperature chosen is not particularly critical. We generally prefer to carry out the reaction at a temperature in the range from room temperature to the boiling point of the solvent, more preferably with heating.

Step H2

The next step in this reaction is to convert the compound of formula (XXVI) to the desired compound of formula (XXVII) by reaction with a halide of formula $R^{7a}X$. The halide is preferably a chloride or bromide.

The reaction is preferably effected in the presence of a solvent, the nature of which is not critical, provided that it has no adverse effect upon the reaction. Examples of suitable solvents include: ethers, such as diethyl ether or ethylene glycol dimethyl ether; ketones, such as acetone or methyl ethyl ketone; and dimethylformamide.

The reaction is also preferably effected in the presence of a base, the major function of which is to react with and thus eliminate from the reaction system the hydrogen halide HX produced in the course of the reaction. Any base capable of doing this without interfering with the reaction may be employed. Suitable bases include: alkali metals, such as sodium or potassium; alkali metal hydrides, such as sodium hydride or potassium hydride; alkali metal amides, such as sodium amide; and alkali metal carbonates, such as sodium carbonate or potassium carbonate.

The reaction will take place over a wide range of temperatures and the precise temperature chosen is not particularly critical. We generally prefer to carry out the reaction at a temperature within the range from room temperature to the boiling point of the solvent, preferably with heating.

METHOD I

Compounds of the invention in which $R^6$ represents a group of formula $-CH_2-W$ and W represents a morpholinomethyl group, that is to say compounds of formula (XXX), may be prepared as illustrated in the following reaction scheme:

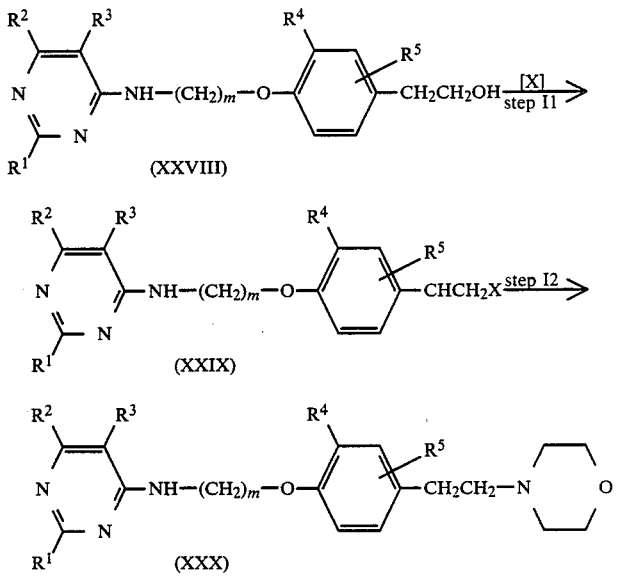

In the above formulae, $R^1$, $R^2$, $R^3$, $R^4$, $R^5$, m, X and [X] are as defined above.

Step I1

In this step, the compound of formula (XXVIII) (which may have been prepared by procedures similar to those described in Method A) is reacted with a halogenating agent [X] to give the compound of formula (XXIX).

This reaction is essentially the same as that described above in step C1 of Method C and may be carried out using the same reagents and under the same reaction conditions.

Step I2

In this step, the halogen compound of formula (XXIX) is reacted with morpholine, to give the desired compound of formula (XXX). This reaction is essentially the same as the reaction described above in step C2 of Method C and may be carried out employing the same solvents and reaction conditions. The preferred solvents are alcohols and the preferred reaction temperature is from room temperature to 150° C., preferably from 120° to 130° C., under superatmospheric pressure.

METHOD J

Compounds in which one or both of $R^2$ and $R^3$ represents a $C_2-C_4$ alkoxyalkyl or alkylthioalkyl group may be prepared as illustrated in the following reaction scheme:

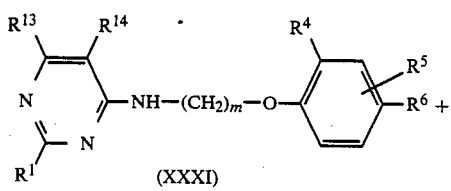

(XXXI)

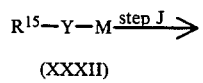

(XXXII)

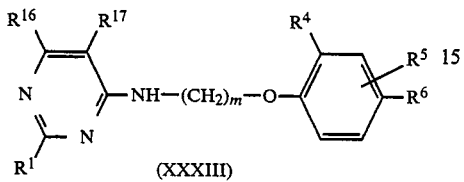

(XXXIII)

In the above formulae, $R^1$, $R^4$, $R^5$, $R^6$, m and Y are as defined above. One or both of $R^{13}$ and $R^{14}$ represents a $C_1$–$C_3$ haloalkyl group; where only one of $R^{13}$ and $R^{14}$ represents such a group, the other represents any of the groups individually defined for $R^2$ or $R^3$. $R^{15}$ represents a $C_1$–$C_3$ alkyl group, provided that the total number of carbon atoms in $R^{15}$ plus a single haloalkyl group represented by $R^{13}$ or $R^{14}$ does not exceed 4. M represents an alkali metal, preferably sodium. One or both of $R^{16}$ and $R^{17}$ represens a $C_2$–$C_4$ alkoxyalkyl or alkylthioalkyl group; where only one of $R^{16}$ and $R^{17}$ represents such a group, the other represents any of the groups individually defined for $R^2$ or $R^3$.

In this reaction, the alkali metal alkoxide or alkanethiolate of formula (XXXII) is reacted with the compound of formula (XXXI) (which may have been prepared following the procedures described in any of the preceding Methods) to give the desired compound of formula (XXXIII). The reaction is preferably effected in the presence of a solvent, the nature of which is not critical, provided that it has no adverse effect upon the reaction. Examples of suitable solvents include: aromatic, aliphatic and cycloaliphatic hydrocarbons, which may or may not be halogenated (e.g. chlorinated) such as benzene, toluene, xylene, methylnaphthalene, petroleum ether, ligroin, hexane chlorobenzene, methylene chloride, chloroform, 1,2-dichloroethane, trichloroethylene or cyclohexane; ethers, such as diethyl ether, ethylene glycol dimethyl ether, tetrahydrofuran or dioxane; and alcohols, such as methanol, ethanol or ethylene glycol.

The reaction will take place over a wide range of temperatures, for example from room temperature to the boiling point of the solvent. In general, heating is preferred.

Following any of the reactions described above, the product may be isolated from the reaction mixture by conventional means. Alternatively, in many cases, subsequent reactions may be carried out without isolation of any intermediate product.

The desired products may, if required, be purified by conventional techniques, such as recrystallization or the various chromatography techniques, notably column chromatography or preparative thin layer chromatography.

If desired, an acid addition salt of the compound of the invention may easily be prepared by introducing an acid into the reaction mixture after completion of the reaction and then removing the solvent.

One of the starting materials employed in Method A, the compound of formula (XXXVII), may be prepared as illustrated in the following reaction scheme:

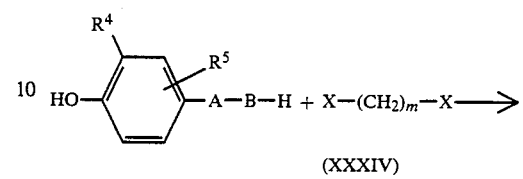

(XXXIV)

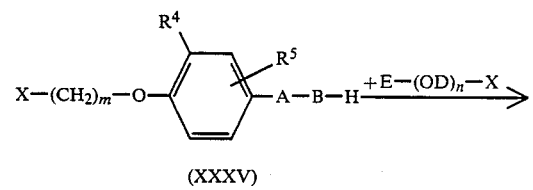

(XXXV)

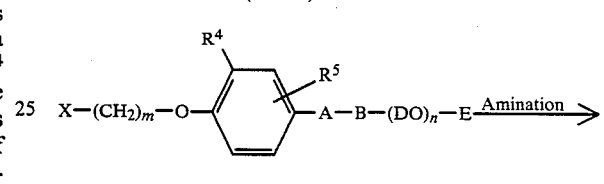

(XXXVI)

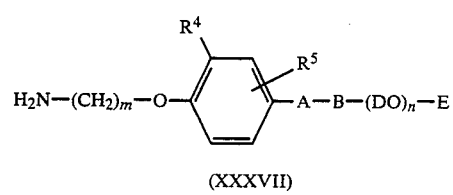

(XXXVII)

In the above formulae, $R^4$, $R^5$, A, B, X, m, E, n and D are as defined above. All of the individual steps involved in this reaction scheme are known per se and may be carried out under conventional conditions.

The compounds of this invention have excellent acaricidal activity against eggs, imagoes and adults of the two-spotted spider mite (*Tetranychus urticae*), the European red mite (*Panonychus ulmi*), the citrus red mite (*Panonychus citri*) and rust mites, etc., which are parasitic on fruit trees, vegetables and flowering plants, and against Ixodidac, Dermanysside and Sarcoptidae etc., which are parasitic on animals. They are also active against Oestrus, Lucilia, Hypoderma, Gautrophilus, etc.; external parasites on animals and birds such as fleas and lice, etc.; domestic insects such as cockroaches, muscids, etc.; as well as various kinds of noxious insects in agriculture and gardening such as aphids, the diamondback moth (*Plutella xylostella*), larvae of Lepidoptera, the green rice leafhopper and the brown rice leafhopper.

Further, the compounds of this invention are active against Meloidogyne, Bursaphelenchus, Phizoglyphus, etc. in the soil.

The compounds of this invention also have a strong fungicidal activity and are effectie for the prevention and extermination of various blights which may occur in agricultural products, such as *Puccinia recondita*, *Sphaerotheca fuliginea*, as well as *Pyricularia oryzae* *Phytophtora infestans*, etc.

The compounds of this invention also have excellent activity against internal parasites in animals and humans and are particularly active against nematods, as well as parasites such as Filariidae and Setariidae, which affect domestic animals, fowls and pets such as swine, sheep, goats, cattle, horses, dogs, cats and chickens, and parasites which may be found in the digestive organs, blood and other tissues or organs in humans.

Reflecting the activity of the present compounds, the invention further provides compositions which contain one or more of the compounds of the invention, together with a carrier and optionally other auxiliary agents, if necessary. The present compositions may be formulated as preparations of the type commonly employed for agricultural use or for use against domestic insect pests, for instance as dusts, coarse dusts, microgranules, fine microgranules, wettable powders, emulsifiable concentrates, aqueous or oily suspensions, and aerosols.

The carrier employed may be natural or synthetic and organic or inorganic; it is generally employed to assist the active ingredient to reach the substrate to be treated, and to make it easier to store, transport or handle the active compound. It may be solid, liquid or gaseous.

Suitable solid carriers include: inorganic substances, such as clays (examples of which are kaolinite, montmorillonite, and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes such as carnauba wax and beeswax; or urea.

Examples of suitable liquid carriers include: paraffinic or naphthenic hydrocarbons, such as kerosene, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform trichloroethylene, monochlorobenzene and o-chlorotoluene; ethers such as dioxane and tetrahydrofuran; ketones, such as acetone, methyl ethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, hexanol, ethylene glycol, diethylene glycol, cyclohexanol, and benzyl alcohol; ether alcohols, such as ethylene glycol monoethyl ether, ethylene glycol monophenyl ether, diethylene glycol monoethyl ether and diethylene glycol monobutyl ether; other polar solvents, such as dimethylformamide and dimethyl sulfoxide; and water.

Suitable gaseous carriers include: air, nitrogen, carbon dioxide and fluorocarbon propellants such as those sold under the Trade Mark "Freon"; they may be mixed in a known manner to give a propellant.

The compositions of the invention may contain one or more surface active agents and/or polymers to improve the properties of the compositions and help them to disperse, emulsify, spread, penetrate and bind or to control disintegration, improve fluidity or impart corrosion resistance to the composition, or to stabilize the active compound. Any of the conventional classes or surface active agent (non-ionic, anionic, cationic or amphoteric) may be employed, but it is preferred to employ non-ionic and/or anionic surface active agents whereby wetting, adhesion and absorption and desired effects may be improved.

Examples of suitable non-ionic surface active agents include: the polymerization adducts of ethylene oxide with higher alcohols, such as lauryl alcohols, stearyl alcohol and oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or dialkylphosphoric acids, such as stearylphosphoric acid or dilauryl phosphoric acid; the polymerization adducts of ethylene oxide with amines, such as dodecylamine; the polymerization adducts of ethylene oxide with higher fatty amides, such as stearamide; higher fatty acid esters of polyhydric alcohols, such as sorbitan, and the polymerization adducts of ethylene oxide therewith; and the polymerization adducts of ethylene oxide with propylene oxide.

Examples of suitable anionic surface active agents include: alkyl sulfate salts, such as sodium lauryl sulfate or oleyl sulfate amine salt; alkyl sulfonate salts, such as sodium dioctyl sulfosuccinate or sodium 2-ethylhexenesulfonate; and aryl sulfonate salts, such as sodium isopropylnaphthalenesulfonate, sodium methylenebisnaphthalenesulfonate, sodium ligninsulfonate or sodium dodecylbenzenesulfonate.

Moreover, the compositions of the present invention may be used in combination with high molecular weight compounds or other formulation agents, such as casein, gelatin, albumin, glue, sodium alginate, carboxymethylcellulose, methylcellulose, hydroxyethylcellulose or polyvinyl, in order to improve the properties and/or to increase the biological effect of the compositions.

The above-mentioned carriers and various auxiliary agents may be used alone or in any desired combination, depending upon the type of preparation, the application and other factors.

For example, dusts may conveniently contain from 1 to 25% by weight of the active compound, the remainder being a solid carrier.

Wettable powders may conveniently contain, for example, from 25 to 90% by weight of the compound, the remainder being a solid carrier and a dispersing and wetting agent, if required, together with a protective colloidal agent, a thixotropic agent and an anti-foaming agent.

Granules may conveniently contain from 1 to 35% by weight of the active compound, a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may be conveniently contain, for example, from 5 to 50% by weight of the active compound and from 5 to 20% by weight of an emulsifying agent, the remainder being a liquid carrier, together with, if required, a corrosion inhibitor.

Oil preparations may conveniently contain from 0.5 to 5% by weight of the active compound, the remainder being a liquid carrier such as kerosene.

Aerosols may conveniently contain from 0.1 to 5% by weight of the active compound and optionally a perfume, the remainder being an oily and/or aqueous carrier, and a propellant such as liquified petroleum gas, a fluorocarbon or carbon dioxide.

The compositions of the invention may be applied, for example, to paddy or other fields before or after emergence of disease in plants or to plants bearing harmful insects and mites; a concentration of from 10 to 500 ppm for the active ingredient is usually suitable, especially for application to leaves and stems of plants and to soil, whereby effective control may be attained.

The composition of the invention may conveniently be blended with other insecticides for a broader insecticidal spectrum and, in some case, a synergistic effect may be expected.

Suitable insecticides include:

phosphorus-containing insecticides: such as O,O-diethyl O-(2-isopropyl-4-methyl-6pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-[2-(ethylthio)ethyl]phosphorodithioate, O,O-dimethyl-1-hydroxy-2,2,2-trichloroethylphosphonate, O,O-diethyl-O-(5-phenyl-3-isoxazolyl)-phosphorothioate, O,O-dimethyl-O-(3-methyl-4-methylmercaptophenyl)thiophosphate, O-ethyl-O-p-cyanophenyl phenylphosphonothioate, O,O-dimethyl S-(1,2-dicarboethoxyethyl)phosphorodithioate, 2-chloro-1-(2,4,5-trichlorophenyl)vinyldimethyl phosphate, 2-chloro-1-(2,4-dichlorophenyl)vinylmethyl phosphate, O,O-dimethyl O-p-cyanophenyl phosphorothioate, 2,2-dichlorovinyldimethylphosphate, ethyl mercaptophenylacetate O,O-dimethyl phosphorodithioate, S-[(6-chloro-2-oxo-3-benzooxazolinyl)methyl]-O,O-diethylphosphorodithioate, 4-methylthiophenyl dipropylphosphate, 2-chloro-1-(2,4-dichloro-phenyl)-vinyldiethylphosphate, O,O-diethyl O-(3-oxo-2-phenyl-2H-pyridazin-6-yl)phosphorothioate, O,O-dimethyl S-(1-methyl-2-ethylsulfinyl)ethyl phosphorothioate, O,O-dimethyl S-phthalimidomethyl phosphorodithioate, dimethylmethylcarbamoylethylthioethyl thiophosphorothioate, O,O-diethyl S-(N-ethoxycarbonyl-N-methylcarbamoylmethyl)phosphorodithioate, O,O-dimethyl-S-[2-methoxy-1,3,4-thiadiazol-5(4H)-onyl-(4)-methyl]dithiophosphate, 2-methoxy-4H-1,3,2-benzodioxaphosphorin 2-sulfide, O,O-diethyl-O-(3,5,6-trichloro-2-pyridyl)phosphorothioate, O,S-dimethyl-N-acetyl phosphoroamidothioate, O-2,4-dichlorophenyl O-ethyl S-propylphosphorodithioate, O,O-diethyl S-(2-chloro-1-phthalimidoethyl)phosphorodithioate and O-6-ethoxy-2-ethylpyrimidin-4-yl O,O-dimethylphosphorothioate;

carbamate-type insecticides; such as 1-naphthyl N-methylcarbamate, S-methyl-N-[methylcarbamoyloxy]-thioacetoimidate, 2-sec-butylphenyl-N-methylcarbamate, 2-isopropoxyphenyl-N-methylcarbamate, 1,3-bis(carbamoylthio)-2-(N,N-dimethylamino)propane hydrochloride and 2-dimethylamino-5,6-dimethylpyrimidin-4-yl dimethylcarbamate;

and other insecticides; such as nicotine sulfate, milbemycin D, 6-methyl-2,3-quinoxalinedithiocyclic S,S-dithiocarbonate, 2,4-dinitro-6-sec-butylphenyldimethylacrylate, 1,1-bis(p-chlorophenyl)-2,2,2-trichloroethanol, azoxybenzene, di(p-chlorophenyl)cyclopropyl carbinol, isopropyl 4,4'-dichlorobenzilate, ethyl 4,4'-dichlorobenzilate, ethyl O-benzoyl-3-chloro-2,6-dimethoxybenzohydroxymate, isopropyl, 4,4'-dibromobenzilate, tricyclohexyltin hydroxide, hexakis(β,β-dimethylphenethyl)distanoxane, 2-(4-t-butylphenoxy)cyclohexylpropinylsulfide, 3-methyl-1,5-bis(2,4-xylyl)-1,3,5-triazapenta-1,4-diene, 2,4,5,4'-tetrachlorodiphenyl sulfone, hexachlorohexahydromethanobenzodioxathiepine oxide, 5-dimethylamino-1,2,3-trithiane hydrogen oxalate and machine oil.

However, the nature of any such additional insecticide is not critical.

The composition of the invention may be blended with fungicides. Suitable fungicides are as follows.

carbamate-type fungicides; such as 3,3'-ethylenebis(tetrahydro-4,6-dimethyl-2H-1,3,5-thiadiazine-2-thione, zinc or manganese ethylenebisdithiocarbamate, bis(-dimethyldithiocarbamoyl)disulfide, zinc propylenebisdithiocarbamate, methyl 1-(butylcarbamoyl)-2-benzimidazolcarbamate, 1,2-bis(3-methoxycarbonyl-2-thioureido)benzene and bisdimethyldithiocarbamoyl zinc ethylenebisdithiocarbamate;

dicarboximide-type fungicides; such as N-trichloromethylthio-4-cyclohexene-1,2-dicarboximide and N-tetrachloroethylthio-4-cyclohexene-1,2-dicarboximide;

oxazine-type fungicides; such as 5,6-dihydro-2-methyl-1,4-oxazine-3-carboxanilide-4,4-dioxide;

naphthoquinone-type fungicides; such as 2,3-dichloro-1,4-naphthoquinone;

and other fungicides; such as 3-hydroxy-5-methylisoxazole, 5-ethoxy-3-trichloromethyl-1,2,4-thiadiazole, 2,4-dichloro-6-(o-chloroanilino)-1,3,5-triazine, 2,3-dicyano-1,4-dithioanthraquinone, copper 8-quinolate, polyoxin, validamycin, tetrachloroisophthalonitrile, 2-(1-methylpropyl)-4,6-dinitrophenol β,β-dimethylacrylate, triphenyltin hydroxide, phytomycin, dinitromethylheptylphenyl crotonate, 5-butyl-2-dimethylamino-6-methyl-pyrimidin-4-ol, 6-(3,5-dichloro-4-methylphenyl)-3-(2H)pyridazinone, 6-(3-bromophenyl)-3-(2H)pyridazinone; N-(2,6-dimethylphenyl)-N-methoxyacetylalanine methyl ester and bis(8-guanidinooctyl)amine acetate.

The preparation of many of the compounds of the invention is illustrated by the following Examples 1 to 21. Subsequently, Examples 22 to 29 illustrate formulations containing the compounds of the invention. The excellent biological activities of the compounds of the invention are then demonstrated by Examples 30 to 36. All refractive indexes reported in the following Examples were measured using the sodium D-line, i.e. all are $n_D$.

EXAMPLE 1

Synthesis of 5-Chloro-4-{2-[4-(2-ethoxyethyl)-2-methylphenoxy]ethylamino}-6-methylpyrimidine (Compound No. 12)

1.6 g of 4,5-dichloro-6-methylpyrimidine was dissolved in 50 ml of toluene. 1.0 g of triethylamine and 2.2 g of 2-[4-(2-ethoxyethyl)-2-methylphenoxy]ethylamine were added to the solution, and the reaction mixture was heated under reflux for 5 hours, whilst stirring. At the end of this time, the reaction mixture was washed with water and dried over anhydrous sodium sulfate. The toluene was removed by distillation under reduced pressure, and the oily product thus obtained was subjected to column chromatography (Wakogel C-200, eluted with a 2:1 by volume mixture of toluene and ethyl acetate) to isolate the product. The crystals thus obtained were recrystallized from hexane to afford 2.6 g of the title compound as colorless needles melting at 57°-58° C.

EXAMPLE 2

Synthesis of 4-{2-[4-(2-allyloxyethyl)-2-methylphenoxy]ethylamino}thieno[2,3-d]pyrimidine (Compound No. 14)

1.0 g of triethylamine and 2.2 g of 2-[4-(2-allyloxyethyl)-2-methylphenoxy]ethylamine were added to 1.7 g of 4-chlorothieno[2,3-d]pyrimidine dissolved in 50 ml of toluene. The mixture was then heated under reflux, whilst stirring, for 3 hours. At the end of this time, the triethylamine hydrochloride thus produced was removed by filtration and toluene was removed from the filtrate by distillation under reduced pressure. The oily substance thus obtained was subjected to column chromatography (Wakogel C-200, eluted with 2:1 by volume mixture of toluene and ethyl acetate) to isolate the product, and the crystals obtained were recrystallized from hexane, to give 3.1 g of the title compound as colorless crystals melting at 78°-80° C.

EXAMPLE 3

Synthesis of 4-{2-[2-methyl-4-(2-methoxypropyl)phenoxy]ethylamino}quinazoline (Compound No. 169)

1.0 g of triethylamine and 2.2 g of 2-[2-methyl-4-(2-methoxypropyl)phenoxy]ethylamine were added to 1.7 g of 4-chloroquinazoline dissolved in 50 ml of toluene. The mixture was then heated under reflux, whilst stirring, for 3 hours. At the end of this time, the reaction product was washed with water and dried over anhydrous sodium sulfate. Toluene was removed by distillation under reduced pressure. The oily product thus obtained was subjected to column chromatography (Wakogel C-200, eluted with a 1:1 by volume mixture of toluene and ethyl acetate) to isolate the product, and the crystals obtained were recrystallized from hexane, to give 2.2 g of the title compound as a colorless crystalline powder, melting at 95°-97° C.

EXAMPLE 4

Synthesis of 5-chloro-2,6-dimethyl-4-{2-[4-(2-ethoxyethyl)-2-methylphenoxy]ethylamino}pyrimidine (Compound No. 15)

1.0 g of triethylamine and 2.2 g of 2-[4-(2-ethoxyethyl)-2-methylphenoxy]ethylamine were added to 1.8 g of 4,5-dichloro-2,6-dimethylpyrimidine dissolved in 50 ml of toluene. The mixture was heated under reflux, whilst stirring, for 5 hours. At the end of this time, the reaction product was washed with water and dried over anhydrous sodium sulfate. Toluene was then removed by distillation under reduced pressure, and the oily product obtained was subjected to column chromatography (Wakogel C-200, eluted with a 2:1 by volume mixture of toluene and etyl acetate) to isolate the product. The crystals obtained were recrystallized from hexane, to give 2.0 g of the title compound as colorless granular crystals melting at 61°-63° C.

EXAMPLE 5

Synthesis of 5-chloro-4-{2-[4-(2-ethoxyethoxymethyl)-2-methylphenoxy]ethylamino}-6-methylpyrimidine (Compound No. 113)

3.1 g of 5-chloro-4-{2-[4-(2-hydroxyethyl)-2-methylphenoxy]ethylamino}-6-methylpyrimidine were dissolved in 50 ml of anhydrous tetrahydrofuran and 0.3 g of sodium hydride (which had been freed from mineral oil by washing with hexane) were added to the solution. The mixture was stirred at room temperature for 30 minutes. 1.7 g of 2-bromoethyl ethyl ether was added to the mixture and it was then stirred, whilst heating, for 3 hours. At the end of this time, any excess of sodium hydride was decomposed by adding ethanol. Water was added to the mixture, and the oily substance which separated was extracted with ethyl acetate. The extract was washed with water and dried over anhydrous sodium sulfate. Ethyl acetate was removed by distillation under reduced pressure to give an oily substance which was subjected to column chromatography (Wakogel C-200, eluted with a 2:1 by volume mixture of toluene and ethyl acetate) to afford 2.0 g of the title compound as a pale yellow oily liquid, $n^{16.4} = 1.5591$.

EXAMPLE 6

Synthesis of 5-chloro-4-{2-[4-(2-ethylaminoethyl)-2-methylphenoxy]ethylamino}-6-methylpyrimidine (Compound No. 111)

1.9 g of 4-{2-[4-(2-bromoethyl)-2-methylphenoxy]ethylamino}-5-chloro-6-methylpyrimidine and 5 ml of a 70% w/v aqueous solution of ethylamine were dissolved in 20 ml of ethanol, and the mixture was charged into an autoclave. The mixture was allowed to react at 120° to 130° C. for 10 hours. At the end of this time, ethanol was removed by distillation under reduced pressure and the oily product obtained was subjected to column chromatography (Wakogel C-200, eluted with ethanol), to afford 1.3 g of the title product as a pale yellow oily liquid, $n^{24.1} = 1.5610$.

EXAMPLE 7

Synthesis of 5-chloro-4-{2-[4-(2-ethylthioethyl)-2-methylphenoxy]ethylamino}-6-methylpyrimidine (Compound No. 109)

0.5 g of the sodium salt of ethyl mercaptan was added to 30 ml of anhydrous tetrahydrofuran. 1.7 g of 5-chloro-4-{2-[4-(2-chloroethyl)-2-methylphenoxy]ethylamino]-6-methylpyrimidine was added to the mixture, which was then heated for 3 hours whilst stirring. At the end of this time, water was added to the mixture, and the oily product which separated was extracted with ethyl acetate. The extract was washed with water and dried over anhydrous sodium sulfate. The ethyl acetate was removed by distillation under reduced pressure. The oily product obtained was subjected to column chromatography (Wakogen C-200, eluted with a 2:1 by volume mixture of toluene and ethyl acetate), to afford 1.2 g of the title compound as a pale yellow oily liquid, $n^{20.8} = 1.5478$.

EXAMPLE 8

Synthesis of
4-{2-[4-(2-ethoxyethyl)-2-methylphenoxy]ethylamino}-5-methylthieno[2,3-d]pyrimidine (Compound No. 146)

4.4 g of 3-cyano-2-ethoxymethyleneamino-4-methylthiophene and 3.8 g of 2-[4-(2-ethoxyethyl)-2-methylphenoxy]ethylamine were dissolved in 50 ml of ethanol, and the solution was heated under reflux for 3 hours, whilst stirring. After cooling, the crystals which separated were collected by filtration and dissolved in 50 ml of ethanol. 0.7 g of sodium ethoxide was added to the solution, and the resulting mixture was heated under reflux for an additional 4 hours. At the end of this time, the ethanol was removed by distillation under reduced pressure.

Water was added to the residue, and the oily substance which separated was extracted with ethyl acetate. The extract was washed with water and dried over sodium sulfate, and then the ethyl acetate was removed by distillation under reduced pressure to obtain an oily substance. This substance was subjected to column chromatography (Wakogel C-200, eluted with a 2:1 by volume mixture of toluene and ethyl acetate), and the crystals obtained were recrystallized from toluene to give 3.1 g of the title compound as a colorless crystalline powder, melting at 55°–57° C.

EXAMPLE 9

Synthesis of
4-{2-[4-(2-ethoxyethyl)-2-methylphenoxy]ethylamino}thieno[2,3-d]pyrimidine oxalate (oxalate of Compound No. 137)

3.6 g of 4-{2-[4-(2-ethoxyethyl)-2-methylphenoxy]ethylamino}thieno[2,3-d]pyrimidine were dissolved in 30 ml of acetone, and 0.9 g of anhydrous oxalic acid dissolved in 30 ml of acetone was added thereto. Reaction occurred at once, and crystals separated. The mixture was stirred for a further 30 minutes whilst heating. The mixture was cooled, and the crystals were collected by filtration and recrystallized from acetone to give 3.9 g of the title compound as colorless columnar crystals melting at 151°–152° C.

EXAMPLE 10

Synthesis of
5-chloro-4-{2-[4-(2-ethoxyethyl)-2-methylphenoxy]ethylamino}-6-methylpyrimidine hydrochloride (hydrochloride of Compound No. 12)

5.0 g of 5-chloro-4-{2-[4-(2-ethoxyethyl)-2-methylphenoxy]ethylamino}-6-methylpyrimidine (powder) were suspended in 10 ml of water, and 5 ml of concentrated aqueous hydrochloric acid were added dropwise thereto. After this addition, the mixture was stirred for 30 minutes, and cooled to separate the crystals. These crystals were collected by filtration and washed with cold water and toluene, in that order, to give 5.2 g of the title compound as colorless needles melting at 123°–124° C.

EXAMPLE 11

Synthesis of
5-chloro-4-{2-[4-(1,3-dioxolan-2-ylmethyl)-2-methylphenoxy]ethylamino}-6-methylpyrimidine (Compound No. 199)

10.0 g of 5-chloro-4-[2-(4-formylmethyl-2-methylphenoxy)ethylamino]-6-methylpyrimidine and 3.0 g of ethylene glycol were dissolved in 300 ml of toluene. A small amount of p-toluenesulfonic acid was added to the solution, and the reaction vessel was equipped with a device for quantitatively determining water. The mixture was then heated under reflux for 8 hours. At the end of this time, the reaction mixture was washed with water and dried over anhydrous sodium sulfate. Toluene was removed by distillation under reduced pressure and the oily product thus obtained was subjected to column chromatography (Wakogel C-200, eluted with a 2:1 by volume mixture of toluene and ethyl acetate) to isolate the product and give 7.9 g of the title compound as a colorless oily liquid, $n^{23.4} = 1.5730$.

EXAMPLE 12

Synthesis of
5-chloro-4-{2-[4-(5,5-dimethyl-1,4-dioxolan-2-ylmethyl)-2-methylphenoxy]ethylamino}-6-methylpyrimidine (Compound No. 211)

6.0 g of 5-chloro-4-{2-[4-(2,3-dihydroxypropyl)-2-methylphenoxy]ethylamino}-6-methylpyrimidine and 50 ml of acetone were dissolved in 200 ml of toluene and a small amount of p-toluenesulfonic acid was added to the solution. The mixture was then heated under reflux for 6 hours. At the end of this time, the reaction mixture was adjusted to weakly alkaline by the addition of a dilute aqueous solution of sodium hydroxide. Then the reaction mixture was washed with water and dried over anhydrous sodium sulfate. Toluene was removed by distillation under reduced pressure. The oily product thus obtained was subjected to column chromatography (Wakogel C-200, eluted with a 2:1 by volume mixture of toluene and ethyl acetate) to isolate the product and give 4.8 g of the title compound as a pale yellow oily liquid, $n^{25.0} = 1.5516$.

EXAMPLE 13

Synthesis of
5-chloro-4-{2-[4-(1,3,2-dioxathiolan-2-oxide-4-ylmethyl)-2-methylphenoxy]ethylamino}-6-methylpyrimidine (Compound No. 216)

2.0 g of 5-chloro-4-{2-[4-(2,3-dihydroxypropyl)-2-methylphenoxy]ethylamino}-6-methylpyrimidine and 1.0 g of pyridine were dissolved in 50 ml of chloroform, and then 0.8 g of thionyl chloride in 10 ml of chloroform was added dropwise, whilst stirring, under ice-cooling. The resultant mixture was then heated under reflux for 2 hours. At the end of this time, the mixture thus obtained was washed successively with water, an aqueous sodium bicarbonate solution and water, and dried over anhydrous sodium sulfate. Toluene was removed by distillation under reduced pressure. The oily substance thus obtained was subjected to column chromatography (Wakogel C-200, eluted with chloroform) to give 1.8 g of the title compound as a colorless oily liquid, $n^{22.0} = 1.5863$.

EXAMPLE 14

Synthesis of
5-chloro-4-{2-[4-(2-ethoxyiminoethyl)-2-methylphenoxy]ethylamino}-6-methylpyrimidine (Compound No. 191)

6.0 g of 5-chloro-4-[2-(4-formylmethyl-2-methylphenoxy)ethylamino]-6-methylpyrimidine were dissolved in 50 ml of ethanol, and a solution of 1.4 g of hydroxylamine hydrochloride in 5 ml of water was added thereto. Subsequently, a solution of 0.8 g of sodium hydroxide in 5 ml of water was added dropwise to the mixture. After completion of the dropwise addition, the mixture was stirred at room temperature for 2 hours. It was then poured into water. Crystals precipitated, and these were collected by filtration, washed with water and dried to obtain 5.2 g of 5-chloro-4-{2-[4-(2-hydroxyiminoethyl)-2-methylphenoxy]ethylamino}-6-methylpyrimidine as an intermediate.

The whole of this intermediate was dissolved in 100 ml of anhydrous tetrahydrofuran. 0.6 g of sodium hydride (from which muineral oil had been eliminated by washing with hexane) was added to the resultant mixture, followed by stirring at room temperature for 30 minutes. Subsequently, 3.6 g of ethyl iodide were added to the mixture, followed by stirring under heating for 2 hours. At the end of this time, excess sodium hydride was decomposed by the addition of ethanol. Water was then added to the mixture, and the resulting oily substance was separated and then extracted with ethyl acetate. The extract was washed with water and dried over anhydrous sodium sulfate, after which the ethyl acetate was removed by distillation under reduced pressure to obtain an oily substance. The oily substance thus obtained was subjected to column chromatography (Wakogel C-200, eluted with a 2:1 by volume mixture of toluene and ethyl acetate), to give 5.1 g of the title compound as a pale yellow oily substance, $n^{23.8} = 1.5478$.

EXAMPLE 15

Synthesis of 5-chloro-4-{2-[4-(2-morpholinoethyl)-2-methylphenoxy]ethylamino}-6-methylpyrimidine (Compound No. 198)

3.0 g of 4-{2-[4-(2-bromoethyl)-2-methylphenoxy]ethylamino}-5-chloro-6-methylpyrimidine and 1.4 g of morpholine were dissolved in 40 ml of ethanol, and the mixture was charged into an autoclave. Then, the mixture was allowed to react at 120° to 130° C. for 8 hours. At the end of this time, the ethanol was removed by distillation and water was added to the residue. The oily substance which separated was then extracted with ethyl acetate. The extract was washed with water and dried over anhydrous sodium sulfate, after which the ethyl acetate was removed by distillation under reduced pressure to obtain an oily substance. The substance obtained was subjected to column chromatography (Wakogel C-200, eluted with ethanol), to obtain 2.6 g of the title compound as a pale yellow oily liquid, $n^{25.7} = 1.5643$.

EXAMPLE 16

Synthesis of 4-{2-[4-(1,3-dioxolan-2-ylmethyl)-2-methylphenoxy]ethylamino}thieno[2,3-d]pyrimidine (Compound No. 230)

1.7 g of 4-chlorothieno[2,3-d]pyrimidine was dissolved in 50 ml of toluene, and 1.0 g of triethylamine and 2.4 g of 2-[4-(1,3-dioxolan-2-ylmethyl)-2-methylphenoxy]ethylamine were added thereto. The mixture was then heated under reflux while stirring for 3 hours. At the end of this time, the triethylamine hydrochloride thus produced was removed by filtration and toluene was removed from the filtrate by distillation under reduced pressure. The oily substance thus obtained was subjected to column chromatography (Wakogel C-200, eluted with a 2:1 by volume mixture of toluene and ethyl acetate) to isolate the product and the crystals thus obtained were recrystallized from hexane to give 2.8 g of the title compound as a colorless crystalline powder, melting at 112°–113° C.

EXAMPLE 17

4-{2-[4-(2-Ethoxyethyl)-2-methylphenoxy]ethylamino}thieno[3,2-d]pyrimidine (Compound No. 244)

1.0 g of triethylamine and 2.2 g of 2-[4-(2-ethoxyethyl)-2-methylphenoxy]ethylamine were added to a solution of 1.7 g of 4-chlorothieno[3,2-d]pyrimidine in 50 ml of toluene, and then the mixture was heated under reflux for 3 hours, whilst stirring. At the end of this time, the triethylamine hydrochloride formed was filtered off and then the toluene was distilled off under reduced pressure from the filtrate to leave an oil. The oil was subjected to column chromatography (Wakogel C-200, eluted with a 1:1 by volume mixture of toluene and ethyl acetate) to give crystals, which were then recrystallized from hexane to give 2.7 g of the title compound in the form of colorless powdery crystals melting at 55°–57° C.

EXAMPLE 18

4-{2-[4-(2-Ethoxyethyl)-2-methylphenoxy]ethylamino}-6-methylfuro[2,3-d]pyrimidine (Compound No. 235)

1.0 g of triethylamine and 2.2 g of 2-[4-(2-ethoxyethyl)-2-methylphenoxy]ethylamine were added to a solution of 1.7 g of 4-chloro-6-methylfuro[2,3-d]pyrimidine in 50 ml of toluene, and then the mixture was heated under reflux for 5 hours, whilst stirring. At the end of this time, the triethylamine hydrochloride formed was filtered off, and then the toluene was distilled off from the filtrate under reduced pressure to leave crystals. The crystals were recrystallized from a mixture of toluene and hexane to give 2.5 g of the title comound in the form of colorless powdery crystals melting at 113°–114° C.

EXAMPLE 19

4-{2-[4-(2-Ethoxyethyl)-2-methylphenoxy]ethylamino}-5,6-dimethylfuro[2,3-d]pyrimidine (Compound No. 234)

A solution of 1.9 g of 3-cyano-4,5-dimethyl-2-ethoxymethyleneiminofuran and 2.2 g of 2-[4-(2-ethoxyethyl)-2-methylphenoxy]ethylamine in 50 ml of ethanol was heated under reflux for 2 hours whilst stirring. 0.7 g of sodium ethoxide was added, and then the mixture was heated under reflux for a further 2 hours. At the end of this time, the reaction mixture was poured into water and the oil which separated was extracted with ethyl acetate. The extract was washed with water and dried over anhydrous sodium sulfate. The ethyl acetate was distilled off under reduced pressure to give an oil, which was subjected to column chromatography (Wakogel C-200, eluted with a 2:1 by volume mixture of toluene and ethyl acetate) to give crystals. These crystals were crystallized from a mixture of toluene and hexane to give 2.2 g of the the title compound in the form of colorless plates melting at 92°–93° C.

EXAMPLE 20

5-Chloro-4-{2-[4-(2-ethoxyethyl)-2-methylphenoxy]ethylamino}-6-methoxymethylpyrimidine (Compound No. 105)

1.0 g of triethylamine and 2.2 g of 2-[4-(2-ethoxyethyl)-2-methylphenoxy]ethylamine were added to a solution of 2.0 g of 6-chloromethyl-4,5-dichloropyrimidine in 50 ml of toluene, and then the mixture was stirred at room temperature for 4 hours. At the end of this time, the triethylamine hydrochloride formed was filtered off and the toluene was distilled off from the filtrate under reduced pressure to give 3.0 g of 5-chloro-6-chloromethyl-4-{2-[4-(2-ethoxyethyl)-2-methylphenoxy]ethylamino}pyrimidine. All of this compound was dissolved in 30 ml of methanol, 0.6 g of sodium methoxide was added, and the mixture was heated under reflux for 2 hours, whilst stirring. At the end of this time, the reaction mixture was poured into water and the oil which separated was extracted with ethyl acetate. The extract was washed with water and dired over anhydrous sodium sulfate. The ethyl acetate was distilled off under reduced pressure to leave an oil, which was subjected to column chromatography (Wakogel C-200, eluted with a 2:1 by volume mixture of toluene and ethyl acetate) to give 2.7 g of the title compound in the form of small granules melting at 39°–41° C.

EXAMPLE 21

5-Chloro-4-{2-[4-(2-ethoxyethyl)-2-methylphenoxy]ethylamino}-2-methylthiomethylpyridine (Compound No. 103)

1.0 g of triethylamine and 2.2 g of 2-[4-(2-ethoxyethyl)-2-methylphenoxy]ethylamine were added to a solution of 2.1 g of 6-chloromethyl-4,5-dichloro-2-methylpyrimidine in 50 ml of toluene, and the mixture was heated under reflux for 3 hours, whilst stirring. At the end of this time, the triethylamine hydrochloride formed was filtered off and the toluene was distilled off from the filtrate under reduced pressure to give 2.8 g of 5-chloro-6-chloromethyl-4-{2-[4-(2-ethoxyethyl)-2-methylphenoxy]ethylamino}pyrimidine. All of this compound was dissolved in 50 ml of methanol, 10 ml of a 15% w/v aqueous solution of sodium methanethiolate were added, and the mixture was heated under reflux for 2 hours, whilst stirring. At the end of this time, the reaction mixture was poured into water and the oil which separated was extracted with ethyl acetate. The extract was washed with water and dried over anhydrous sodium sulfate. The ethyl acetate was distilled off under reduced pressure to give an oil, which was subjected to column chromatography (Wakogel C-200, eluted with a 2:1 by volume mixture of toluene and ethyl acetate) to give 2.2 g of the title compound in the form of a pale yellow oil, $n^{31.3} = 1.5612$.

Following the appropriate procedures essentially as described in the foregoing Examples, the following compounds of the invention were also prepared. The compounds are identified by the numbers assigned to them in the foregoing Tables 1–11:

| Compound No. | Physical Property |
| --- | --- |
| 1 | m.p. 48–51° C. |
| 2 | $n^{26} = 1.5700$ |
| 3 | $n^{23} = 1.5650$ |
| 4 | $n^{25.2} = 1.5496$ |
| 5 | $n^{18.6} = 1.5528$ |
| 6 | $n^{18} = 1.5506$ |
| 7 | $n^{21.4} = 1.5657$ |
| 8 | $n^{22.2} = 1.5768$ |
| 9 | m.p. 70–72° C. |
| 10 | $n^{25.8} = 1.5718$ |
| 11 | m.p. 94–96° C. |
| 13 | m.p. 72–74° C. |
| 14 | $n^{27.2} = 1.5504$ |
| 16 | m.p. 63–64° C. |
| 17 | m.p. 79–81° C. |
| 18 | m.p. 40–42° C. |
| 19 | m.p. 58–60° C. |
| 20 | m.p. 49–50° C. |
| 21 | $n^{20.8} = 1.5508$ |
| 22 | m.p. 72–74° C. |
| 23 | m.p. 78–80° C. |
| 24 | m.p. 54–56° C. |
| 25 | $n^{27.2} = 1.5545$ |
| 26 | $n^{23.2} = 1.5540$ |
| 27 | $n^{23.4} = 1.5535$ |
| 28 | $n^{22.0} = 1.5568$ |
| 29 | $n^{23.8} = 1.5520$ |
| 30 | $n^{18.6} = 1.5304$ |
| 31 | $n^{22.2} = 1.5440$ |
| 32 | $n^{26.2} = 1.5583$ |
| 33 | $n^{28.2} = 1.5508$ |
| 34 | $n^{22.2} = 1.5621$ |
| 35 | $n^{28.6} = 1.5598$ |
| 36 | $n^{22.8} = 1.5526$ |
| 37 | $n^{25.4} = 1.5459$ |
| 38 | $n^{25.1} = 1.5460$ |
| 39 | $n^{21.8} = 1.5549$ |
| 40 | $n^{20.0} = 1.5538$ |
| 41 | m.p. 53–54° C. |
| 42 | $n^{27.6} = 1.5519$ |
| 43 | $n^{26.0} = 1.5423$ |
| 44 | $n^{24.2} = 1.5584$ |
| 45 | $n^{26.0} = 1.5528$ |
| 46 | $n^{22.0} = 1.5418$ |
| 47 | $n^{23.0} = 1.5535$ |
| 48 | $n^{23.5} = 1.5442$ |
| 49 | $n^{26.3} = 1.5500$ |
| 50 | $n^{18.0} = 1.5704$ |
| 51 | $n^{18.2} = 1.5594$ |
| 52 | m.p. 74–76° C. |
| 53 | $n^{25.8} = 1.5640$ |
| 54 | $n^{23.0} = 1.5553$ |
| 55 | $n^{24.2} = 1.5543$ |
| 56 | $n^{22.0} = 1.5541$ |
| 57 | $n^{22.2} = 1.5580$ |
| 58 | $n^{25.6} = 1.5518$ |
| 59 | $n^{19.4} = 1.5727$ |
| 60 | $n^{15.0} = 1.5762$ |
| 61 | $n^{28.7} = 1.5615$ |
| 62 | $n^{23.0} = 1.5603$ |
| 63 | $n^{20.8} = 1.5908$ |
| 64 | $n^{28.8} = 1.5747$ |
| 65 | m.p. 48–51° C. |
| 66 | $n^{18.0} = 1.5930$ |
| 67 | $n^{17.4} = 1.5874$ |
| 68 | $n^{27.2} = 1.5676$ |
| 69 | $n^{28.4} = 1.5750$ |
| 70 | $n^{28.8} = 1.5684$ |
| 71 | m.p. 77–78° C. |
| 72 | $n^{24.0} = 1.5448$ |
| 73 | m.p. 50–51° C. |
| 74 | $n^{24.2} = 1.5494$ |
| 75 | m.p. 69–71° C. |
| 76 | m.p. 51–54° C. |
| 77 | $n^{26.7} = 1.5725$ |
| 78 | $n^{26.4} = 1.5594$ |
| 79 | $n^{26.4} = 1.5480$ |
| 80 | $n^{26.4} = 1.5428$ |
| 81 | $n^{26.4} = 1.5576$ |
| 82 | $n^{25.2} = 1.5363$ |
| 83 | $n^{25.2} = 1.5421$ |
| 84 | $n^{25.2} = 1.5658$ |
| 85 | $n^{26.6} = 1.5643$ |
| 86 | m.p. 57–59° C. |

| Compound No. | Physical Property |
|---|---|
| 87 | m.p. 50–52° C. |
| 88 | m.p. 59–60° C. |
| 89 | m.p. 56–58° C. |
| 90 | m.p. 55–57° C. |
| 91 | $n^{26.4} = 1.5491$ |
| 92 | m.p. 69–71° C. |
| 93 | $n^{26.5} = 1.5704$ |
| 94 | $n^{26.6} = 1.5396$ |
| 95 | $n^{26.4} = 1.5443$ |
| 96 | $n^{26.6} = 1.5720$ |
| 97 | $n^{27.4} = 1.5476$ |
| 98 | m.p. 63–64° C. |
| 99 | m.p. 81–82° C. |
| 100 | $n^{19.0} = 1.5896$ |
| 101 | m.p. 75–76° C. |
| 102 | $n^{24.8} = 1.5578$ |
| 104 | $n^{30.6} = 1.5469$ |
| 106 | m.p. 38–40° C. |
| 107 | $n^{28.5} = 1.5602$ |
| 108 | $n^{21.8} = 1.5852$ |
| 110 | $n^{24.2} = 1.5607$ |
| 112 | $n^{27.2} = 1.5474$ |
| 114 | $n^{25.4} = 1.5406$ |
| 115 | $n^{22.0} = 1.5552$ |
| 116 | $n^{22.2} = 1.5582$ |
| 117 | $n^{28.8} = 1.5530$ |
| 118 | $n^{21.8} = 1.5544$ |
| 119 | $n^{23.2} = 1.5481$ |
| 120 | $n^{26.0} = 1.5360$ |
| 121 | $n^{25.2} = 1.5395$ |
| 122 | $n^{26.2} = 1.5505$ |
| 123 | $n^{28.8} = 1.5664$ |
| 124 | $n^{27.4} = 1.5406$ |
| 125 | $n^{20.0} = 1.5450$ |
| 126 | $n^{23.8} = 1.5444$ |
| 127 | $n^{25.8} = 1.5484$ |
| 128 | $n^{23.0} = 1.5450$ |
| 129 | $n^{21.8} = 1.5400$ |
| 130 | $n^{22.2} = 1.5334$ |
| 131 | $n^{20.8} = 1.5882$ |
| 132 | m.p. 73–75° C. |
| 133 | $n^{22.0} = 1.5638$ |
| 134 | m.p. 56–58° C. |
| 135 | m.p. 92–94° C. |
| 136 | m.p. 81–83° C. |
| 137 | m.p. 77–79° C. |
| 138 | m.p. 87–90° C. |
| 139 | m.p. 87–89° C. |
| 140 | m.p. 84–86° C. |
| 142 | m.p. 62–64° C. |
| 143 | m.p. 66–69° C. |
| 144 | m.p. 111–112° C. |
| 145 | m.p. 57–60° C. |
| 147 | m.p. 71–75° C. |
| 148 | $n^{24.6} = 1.6145$ |
| 149 | m.p. 56–58° C. |
| 150 | m.p. 94–75° C. |
| 151 | m.p. 75–76° C. |
| 152 | m.p. 84–85° C. |
| 153 | m.p. 81–83° C. |
| 154 | m.p. 64–66° C. |
| 155 | $n^{25.7} = 1.5648$ |
| 156 | m.p. 106–107° C. |
| 157 | m.p. 89–90° C. |
| 158 | m.p. 62–64° C. |
| 160 | m.p. 99–101° C. |
| 161 | m.p. 128–130° C. |
| 162 | m.p. 134–135° C. |
| 163 | m.p. 118–120° C. |
| 164 | m.p. 99–101° C. |
| 165 | m.p. 109–111° C. |
| 166 | m.p. 120–122° C. |
| 167 | m.p. 94–95° C. |
| 168 | m.p. 78–80° C. |
| 170 | m.p. 97–99° C. |
| 171 | m.p. 83–85° C. |
| 172 | m.p. 80–82° C. |
| 173 | m.p. 86–89° C. |
| 174 | m.p. 98–99° C. |
| 175 | m.p. 118–120° C. |
| 176 | m.p. 124–125° C. |
| 177 | m.p. 86–88° C. |
| 178 | m.p. 100–102° C. |
| 179 | $n^{26.4} = 1.6062$ |
| 180 | m.p. 114–115° C. |
| 181 | m.p. 109–112° C. |
| 182 | m.p. 103–106° C. |
| 183 | m.p. 106–108° C. |
| 184 | m.p. 107–108° C. |
| 185 | m.p. 96–98° C. |
| 186 | $n^{25.8} = 1.5541$ |
| 187 | $n^{22.2} = 1.5684$ |
| 188 | $n^{20.0} = 1.5587$ |
| 190 | $n^{23.8} = 1.5564$ |
| 192 | $n^{19.6} = 1.5721$ |
| 193 | $n^{20.6} = 1.5648$ |
| 194 | $n^{19.6} = 1.5625$ |
| 195 | $n^{28.8} = 1.5514$ |
| 196 | $n^{29.0} = 1.5704$ |
| 197 | $n^{25.2} = 1.5754$ |
| 200 | m.p. 99–100° C. |
| 201 | $n^{23.6} = 1.5672$ |
| 202 | $n^{26.0} = 1.5533$ |
| 203 | $n^{26.7} = 1.5543$ |
| 204 | $n^{22.4} = 1.5514$ |
| 205 | $n^{29.0} = 1.5569$ |
| 206 | $n^{22.4} = 1.5520$ |
| 207 | m.p. 68–70° C. |
| 208 | m.p. 64–66° C. |
| 209 | $n^{28.8} = 1.5737$ |
| 210 | $n^{26.8} = 1.6147$ |
| 212 | m.p. 87–89° C. |
| 213 | $n^{18.6} = 1.5504$ |
| 214 | $n^{17.0} = 1.5491$ |
| 215 | $n^{31.0} = 1.5812$ |
| 217 | $n^{26.0} = 1.5660$ |
| 218 | m.p. 74–75° C. |
| 219 | $n^{26.0} = 1.5648$ |
| 220 | $n^{30.8} = 1.5571$ |
| 221 | m.p. 107–109° C. |
| 222 | $n^{26.2} = 1.5548$ |
| 223 | $n^{27.5} = 1.5620$ |
| 224 | m.p. 94–96° C. |
| 225 | m.p. 78–80° C. |
| 226 | $n^{17.5} = 1.5615$ |
| 227 | $n^{21.4} = 1.5635$ |
| 228 | $n^{21.6} = 1.5782$ |
| 229 | $n^{23.2} = 1.5626$ |
| 231 | m.p. 131–133° C. |
| 232 | m.p. 119–120° C. |
| 233 | m.p. 136–139° C. |
| 236 | m.p. 59–61° C. |
| 237 | $n^{22.2} = 1.5832$ |
| 238 | m.p. 61–63° C. |
| 239 | m.p. 67–68° C. |
| 240 | m.p. 53–54° C. |
| 241 | m.p. 63–64° C. |
| 242 | m.p. 75–76° C. |
| 243 | m.p. 104–106° C. |
| 245 | m.p. 81–83° C. |
| 246 | m.p. 87–89° C. |
| 247 | m.p. 62–63° C. |
| 248 | m.p. 45–47° C. |
| 249 | m.p. 98–100° C. |
| 250 | m.p. 88–90° C. |
| 251 | m.p. 91–92° C. |

EXAMPLE 22

Dust 5 parts by weight of Compound No. 63, 50 parts of talc and 45 parts of kaolin were homogeneously mixed to obtain a dust.

EXAMPLE 23

Wettable powder 69 parts by weight of Compound No. 157, 10 parts of diatomaceous earth, 15 parts of white carbon, 3 parts of sodium ligninsulfonate, 2 parts of Newcol 1106 (trade name, produced by Nippon Nyukazai K.K.) and 1 part of polyvinyl alcohol were homogeneously mixed in a mixer and pulverized by a hammer mill three times to obtain a wettable powder.

EXAMPLE 24

Wettable Powder 25 parts by weight of Compound No. 12, 48 parts of clay, 20 parts of white carbon, 5 parts of a condensation product of formalin with sodium naphthalenesulfonate and 2 parts of polyoxyethylene nonylphenol ether were homogeneously mixed in a mixer and pulverized by a hammer mill three times to obtain a wettable powder.

EXAMPLE 25

Emulsifiable concentrate 20 parts by weight of Compound No. 22 were mixed with 10 parts of Sorpol SM-200 (registered trademark of Toho Kagaku K.K.) and 70 parts of xylene, and the mixture was mixed well with stirring to obtain an emulsifiable concentrate.

EXAMPLE 26

Dust 5 parts by weight of Compound No. 233, 50 parts of talc and 45 parts of kaolin were homogeneously mixed to obtain a dust.

EXAMPLE 27

Wettable powder 69 parts by weight of Compound No. 191, 10 parts of diatomaceous earth, 15 parts of white carbon, 3 parts of sodium ligninsulfonate, 2 parts of Newcol 1106 (trade name, produced by Nippon Nyukazai K.K.) and 1 part of polyvinyl alcohol were homogeneously mixed in a mixer and pulverized by a hammer mill three times to obtain a wettable powder.

EXAMPLE 28

Wettable powder 25 parts by weight of Compound No. 233, 48 parts of clay, 20 parts of white carbon, 5 parts of a condensation product of formalin with sodium naphthalenesulfonate and 2 parts of polyoxyethylene nonylphenol ether were homogeneously mixed in a mixer and pulverized by a hammer mill three times to obtain a wettable powder.

EXAMPLE 29

Emulsifiable concentrate 10 parts by weight of Sorpol SM-200 (registered trademark of Toho Kagaku K.K.) and 70 parts of xylene were mixed with 20 parts of Compound No. 233, and the mixture was mixed well with stirring to obtain an emulsifiable concentrate.

BIOLOGICAL ACTIVITY

In the tests for biological activity given hereafter in Examples 30 to 36, the test compounds were formulated as wettable powders containing 25% by weight of the test compound and produced as described in foregoing Examples 24 and 28. These wettable powders were then diluted to the appropriate concentration, as described hereinafter in these Examples.

EXAMPLE 30

Acaricidal activity against adults of the species *Panonychus citri*

Test solutions each containing 30 ppm of one of the compounds of the invention in admixture with 0.01% w/v of a spreader were prepared. Mulberry leaves were infected with adult red citrus mites (*Panonychus citri*). After infection, the leaves were sprayed with the test solutions, air-dried and then left to stand in a room maintained at 25° C.

After 72 hours, the percentage kill was assessed for each treatment group. A percentage kill of 100% is reported as an acaricidal activity of 5, whilst a percentage kill of from 99 to 80% is reported as an acaricidal activity of 4. All of the compounds of the invention tested killed at least 80% of the mites.

The average number of mites in each treatment group was 50.

The results are shown in Table 12.

TABLE 12

| Compound No. | Acaricidal activity |
|---|---|
| 2 | 4 |
| 3 | 5 |
| 5 | 5 |
| 6 | 4 |
| 9 | 5 |
| 11 | 5 |
| 12 | 5 |
| Hydrochloride of 12 | 5 |
| Nitrate of 12 | 5 |
| Phosphate of 12 | 5 |
| Perchlorate of 12 | 5 |
| Phthalate of 12 | 5 |
| p-toluenesulfonate of 12 | 5 |
| Oxalate of 12 | 5 |
| ½ Malonate of 12 | 5 |
| ½ Fumarate of 12 | 5 |
| Fumarate of 12 | 5 |
| Succinate of 12 | 5 |
| Glutarate of 12 | 5 |
| Adipate of 12 | 5 |
| Maleate of 12 | 5 |
| Citrate of 12 | 5 |
| 15 | 5 |
| Hydrochloride of 15 | 5 |
| Oxalate of 15 | 5 |
| 16 | 5 |
| 19 | 5 |
| 20 | 5 |
| 21 | 5 |
| 22 | 5 |
| Oxalate of 22 | 5 |
| 23 | 5 |
| 24 | 4 |
| 25 | 5 |
| 28 | 5 |
| 29 | 5 |
| 30 | 5 |
| 31 | 4 |
| 33 | 5 |
| 34 | 5 |
| 35 | 5 |
| 36 | 5 |
| 37 | 5 |
| 38 | 4 |
| 39 | 5 |
| 40 | 5 |
| 41 | 5 |
| 42 | 4 |

TABLE 12-continued

| Compound No. | Acaricidal activity |
|---|---|
| 43 | 4 |
| 44 | 5 |
| 45 | 5 |
| 47 | 5 |
| 48 | 5 |
| 50 | 5 |
| 51 | 5 |
| 54 | 5 |
| 55 | 4 |
| 57 | 4 |
| 58 | 4 |
| 59 | 5 |
| 60 | 5 |
| 61 | 5 |
| 62 | 5 |
| 63 | 5 |
| 64 | 5 |
| 66 | 4 |
| 67 | 5 |
| 69 | 5 |
| 70 | 5 |
| 71 | 5 |
| 72 | 5 |
| 73 | 5 |
| 74 | 5 |
| 75 | 5 |
| 76 | 5 |
| 77 | 5 |
| 78 | 5 |
| 79 | 5 |
| 80 | 5 |
| 81 | 5 |
| 82 | 5 |
| 83 | 5 |
| 84 | 5 |
| 85 | 5 |
| 86 | 5 |
| 87 | 5 |
| 88 | 5 |
| 89 | 5 |
| 90 | 5 |
| 91 | 5 |
| 92 | 5 |
| 93 | 5 |
| 94 | 5 |
| 95 | 5 |
| 96 | 5 |
| 97 | 5 |
| 98 | 5 |
| 99 | 5 |
| 100 | 5 |
| 101 | 5 |
| 102 | 5 |
| 103 | 5 |
| 104 | 5 |
| 105 | 5 |
| 106 | 5 |
| 107 | 5 |
| 108 | 4 |
| 109 | 5 |
| 111 | 5 |
| 112 | 4 |
| 113 | 5 |
| 114 | 4 |
| 115 | 5 |
| 116 | 5 |
| 117 | 5 |
| 118 | 5 |
| 119 | 5 |
| 120 | 5 |
| 121 | 5 |
| 122 | 4 |
| 123 | 4 |
| 124 | 5 |
| 125 | 5 |
| 127 | 5 |
| 128 | 5 |
| 129 | 5 |
| 130 | 5 |
| 132 | 5 |
| 133 | 5 |
| 134 | 5 |
| 135 | 5 |
| 136 | 5 |
| 137 | 5 |
| Hydrochloride of 137 | 5 |
| Nitrate of 137 | 5 |
| Oxalate of 137 | 5 |
| Adipate of 137 | 5 |
| Fumarate of 137 | 5 |
| 139 | 5 |
| 140 | 5 |
| 141 | 5 |
| 142 | 5 |
| 143 | 5 |
| 144 | 5 |
| 145 | 5 |
| 146 | 5 |
| Oxalate of 146 | 5 |
| 148 | 5 |
| 149 | 5 |
| 150 | 5 |
| 151 | 5 |
| 152 | 4 |
| 153 | 5 |
| 154 | 5 |
| 155 | 5 |
| 156 | 5 |
| 157 | 5 |
| 158 | 5 |
| 160 | 5 |
| 161 | 5 |
| 164 | 5 |
| Hydrochloride of 164 | 5 |
| Nitrate of 164 | 5 |
| Oxalate of 164 | 5 |
| 165 | 4 |
| 167 | 5 |
| 168 | 5 |
| 169 | 5 |
| 170 | 5 |
| 171 | 5 |
| 172 | 5 |
| 173 | 5 |
| 174 | 5 |
| 176 | 5 |
| 179 | 5 |
| 180 | 5 |
| 181 | 5 |
| 182 | 4 |
| 183 | 5 |
| 184 | 5 |
| 185 | 5 |
| 186 | 5 |
| 190 | 4 |
| 191 | 5 |
| Oxalate of 191 | 5 |
| Hydrochloride of 191 | 5 |
| Nitrate of 191 | 5 |
| Fumarate of 191 | 5 |
| Adipate of 191 | 5 |
| p-Toluenesulfonate of 191 | 5 |
| 192 | 5 |
| 193 | 5 |
| 194 | 5 |
| 195 | 4 |
| 196 | 5 |
| 197 | 4 |
| 198 | 4 |
| 199 | 5 |
| Oxalate of 199 | 5 |
| Fumarate of 199 | 5 |
| Adipate of 199 | 5 |
| p-Toluenesulfonate of 199 | 5 |
| 200 | 4 |
| 201 | 5 |
| 202 | 5 |
| 203 | 5 |

TABLE 12-continued

| Compound No. | Acaricidal activity |
| --- | --- |
| 204 | 5 |
| 205 | 5 |
| Oxalate of 205 | 5 |
| Fumarate of 205 | 5 |
| Adipate of 205 | 5 |
| p-Toluenesulfonate of 205 | 5 |
| 206 | 5 |
| 207 | 5 |
| 208 | 5 |
| 209 | 5 |
| 210 | 4 |
| 211 | 5 |
| 212 | 5 |
| Oxalate of 212 | 5 |
| 213 | 5 |
| 214 | 4 |
| 215 | 4 |
| 216 | 5 |
| 217 | 5 |
| 218 | 5 |
| 219 | 5 |
| 220 | 5 |
| 221 | 4 |
| 222 | 5 |
| 223 | 5 |
| Oxalate of 223 | 5 |
| Fumarate of 223 | 5 |
| Adipate of 223 | 5 |
| p-Toluenesulfonate of 223 | 5 |
| 224 | 5 |
| 225 | 5 |
| 226 | 5 |
| 227 | 5 |
| 228 | 5 |
| 229 | 5 |
| 230 | 5 |
| 231 | 5 |
| 232 | 5 |
| 233 | 5 |
| 234 | 5 |
| 235 | 4 |
| 236 | 5 |
| 237 | 5 |
| 238 | 5 |
| 239 | 5 |
| 240 | 5 |
| 241 | 5 |
| 242 | 5 |
| 243 | 5 |
| 244 | 5 |
| 245 | 5 |
| 246 | 5 |
| 247 | 5 |
| 248 | 5 |
| 249 | 5 |
| 250 | 5 |
| 251 | 4 |

EXAMPLE 31

Ovicidal activity against eggs of the species *Panonychus citri*

Test solutions each containing 30 ppm of one of the compounds of the invention in admixture with 0.01% w/v of a spreader were prepared. Mulberry leaves were infected with eggs of the red citrus mite (*Panonychus citri*). After infection, the leaves were sprayed with the test solutions, air-dried and then left to stand in a room maintained at 25° C.

After two weeks, the percentage kill was assessed for each treatment group. A percentage kill of 100% is reported as an ovicidal activity of 5, whilst a percentage kill of from 99 to 80% is reported as an ovicidal activity of 4. All of the compounds of the invention tested killed at least 80% of the eggs.

TABLE 13

| Compound No. | Ovicidal Activity |
| --- | --- |
| 1 | 4 |
| 2 | 5 |
| 3 | 5 |
| 4 | 5 |
| 5 | 5 |
| 6 | 5 |
| 7 | 5 |
| 8 | 5 |
| 9 | 5 |
| 10 | 5 |
| 11 | 5 |
| 12 | 5 |
| Hydrochloride of 12 | 5 |
| Nitrate of 12 | 5 |
| Phosphate of 12 | 5 |
| Perchlorate of 12 | 5 |
| Phthalate of 12 | 5 |
| p-toluenesulfonate of 12 | 5 |
| Oxalate of 12 | 5 |
| ½ Fumarate of 12 | 5 |
| Fumarate of 12 | 5 |
| Succinate of 12 | 5 |
| Glutarate of 12 | 5 |
| Adipate of 12 | 5 |
| Maleate of 12 | 5 |
| Citrate of 12 | 5 |
| 13 | 5 |
| 14 | 4 |
| 15 | 5 |
| 16 | 5 |
| 17 | 5 |
| 18 | 5 |
| 19 | 5 |
| 20 | 5 |
| 21 | 4 |
| 22 | 5 |
| Oxalate of 22 | 5 |
| 23 | 4 |
| 25 | 5 |
| 26 | 5 |
| 27 | 4 |
| 28 | 5 |
| 29 | 5 |
| 30 | 4 |
| 31 | 5 |
| 32 | 5 |
| 33 | 5 |
| 34 | 5 |
| 35 | 5 |
| 36 | 5 |
| 37 | 5 |
| 38 | 5 |
| 39 | 5 |
| 40 | 5 |
| 41 | 5 |
| 42 | 4 |
| 43 | 4 |
| 44 | 5 |
| 45 | 5 |
| 46 | 5 |
| 47 | 5 |
| 48 | 5 |
| 49 | 5 |
| 50 | 5 |
| 51 | 5 |
| 52 | 5 |
| 53 | 5 |
| 54 | 5 |
| 55 | 5 |
| 56 | 4 |
| 57 | 5 |
| 58 | 5 |
| 59 | 5 |
| 60 | 4 |
| 61 | 5 |
| 63 | 5 |
| 67 | 4 |
| 69 | 5 |

TABLE 13-continued

| Compound No. | Ovicidal Activity |
|---|---|
| 71 | 5 |
| 72 | 5 |
| 73 | 5 |
| 74 | 5 |
| 75 | 5 |
| 76 | 5 |
| 77 | 5 |
| 78 | 5 |
| 79 | 5 |
| 80 | 5 |
| 81 | 5 |
| 82 | 5 |
| 83 | 5 |
| 84 | 4 |
| 85 | 5 |
| 86 | 5 |
| 87 | 5 |
| 88 | 5 |
| 89 | 5 |
| 90 | 5 |
| 91 | 5 |
| 92 | 5 |
| 93 | 5 |
| 94 | 5 |
| 95 | 5 |
| 96 | 5 |
| 97 | 5 |
| 98 | 5 |
| 99 | 5 |
| 100 | 4 |
| 101 | 5 |
| 102 | 5 |
| 103 | 4 |
| 104 | 4 |
| 105 | 5 |
| 106 | 4 |
| 108 | 4 |
| 109 | 5 |
| 110 | 4 |
| 113 | 5 |
| 114 | 5 |
| 115 | 5 |
| 116 | 5 |
| 117 | 5 |
| 118 | 5 |
| 119 | 4 |
| 120 | 5 |
| 121 | 5 |
| 122 | 5 |
| 123 | 5 |
| 124 | 5 |
| 125 | 5 |
| 126 | 5 |
| 127 | 5 |
| 128 | 5 |
| 129 | 5 |
| 130 | 5 |
| 132 | 5 |
| 133 | 5 |
| 134 | 5 |
| 135 | 5 |
| 136 | 5 |
| 137 | 5 |
| Hydrochloride of 137 | 5 |
| Nitrate of 137 | 5 |
| Oxalate of 137 | 5 |
| Adipate of 137 | 5 |
| Fumarate of 137 | 5 |
| 142 | 5 |
| 143 | 5 |
| 145 | 5 |
| 146 | 5 |
| Oxalate of 146 | 5 |
| 147 | 5 |
| 148 | 4 |
| 149 | 4 |
| 150 | 5 |
| 151 | 5 |
| 152 | 4 |
| 153 | 5 |
| 154 | 5 |
| 155 | 5 |
| 157 | 5 |
| 161 | 5 |
| 162 | 4 |
| 163 | 5 |
| Hydrochloride of 164 | 5 |
| Nitrate of 164 | 5 |
| Oxalate of 164 | 5 |
| 166 | 5 |
| 170 | 4 |
| 171 | 5 |
| 172 | 5 |
| 174 | 4 |
| 175 | 4 |
| 181 | 5 |
| 185 | 5 |
| 186 | 5 |
| 190 | 5 |
| 191 | 5 |
| Oxalate of 191 | 5 |
| Hydrochloride of 191 | 5 |
| Nitrate of 191 | 5 |
| Fumarate of 191 | 5 |
| Adipate of 191 | 5 |
| p-Toluenesulfonate of 191 | 5 |
| 192 | 5 |
| 193 | 5 |
| 194 | 5 |
| 195 | 4 |
| 196 | 5 |
| 197 | 4 |
| 198 | 4 |
| 199 | 5 |
| Oxalate of 199 | 5 |
| Fumarate of 199 | 5 |
| Adipate of 199 | 5 |
| p-Toluenesulfonate of 199 | 5 |
| 200 | 4 |
| 201 | 5 |
| 202 | 5 |
| 203 | 5 |
| 204 | 4 |
| 205 | 5 |
| Oxalate of 205 | 5 |
| Fumarate of 205 | 5 |
| Adipate of 205 | 5 |
| p-Toluenesulfonate of 205 | 5 |
| 206 | 5 |
| 207 | 5 |
| 208 | 5 |
| 209 | 4 |
| 210 | 4 |
| 211 | 5 |
| 212 | 5 |
| Oxalate of 212 | 5 |
| 213 | 4 |
| 214 | 4 |
| 215 | 4 |
| 216 | 5 |
| 217 | 5 |
| 218 | 5 |
| 219 | 5 |
| 220 | 5 |
| 221 | 5 |
| 222 | 5 |
| 223 | 5 |
| Oxalate of 223 | 5 |
| Fumarate of 223 | 5 |
| Adipate of 223 | 5 |
| p-Toluenesulfonate of 223 | 5 |
| 224 | 4 |
| 225 | 5 |
| 226 | 5 |
| 227 | 5 |
| 228 | 5 |
| 229 | 5 |
| 230 | 4 |
| 231 | 5 |
| 232 | 4 |
| 233 | 4 |
| 234 | 5 |

TABLE 13-continued

| Compound No. | Ovicidal Activity |
|---|---|
| 235 | 5 |
| 236 | 5 |
| 237 | 5 |
| 238 | 5 |
| 239 | 5 |
| 240 | 5 |
| 241 | 5 |
| 242 | 5 |
| 243 | 5 |
| 244 | 5 |
| 245 | 5 |
| 246 | 5 |
| 247 | 5 |
| 248 | 5 |
| 249 | 5 |
| 250 | 5 |
| 251 | 4 |

EXAMPLE 32

Acaricidal and Ovicidal activity against *Panonychus citri*

The test was carried out essentially as described in Examples 30 and 31, except that the concentration of the test compound was 10 ppm or 3 ppm.

The acaricidal and ovicidal activities were assessed after 72 hours and 2 weeks, respectively, as in Examples 30 and 31.

In addition to the compounds of the invention, the test was also carried out on various known compounds of similar structure (referred to as "Control") and these results are also given.

The Control compounds tested may be represented by the formula:

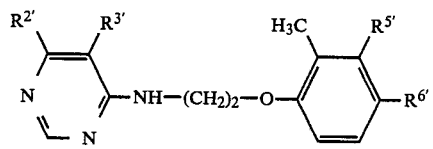

where:

| Control No. | $R^{2'}$ | $R^{3'}$ | $R^{5'}$ | $R^{6'}$ |
|---|---|---|---|---|
| 1 | Me | Cl | H | Bu |
| 2 | Me | Cl | H | Pn |
| 3 | Me | Cl | H | hexyl |
| 4 | Me | Cl | H | All |
| 5 | Me | Cl | H | 2-butenyl |
| 16 | Et | Cl | H | Me |
| 17 | Et | Cl | Me | All |

| Control No. | $R^{2'} + R^{3'}$ | $R^{5'}$ | $R^{6'}$ |
|---|---|---|---|
| 6 | -CH$_2$CH$_2$CH$_2$- | H | Bu |
| 7 | -CH$_2$CH$_2$CH$_2$- | H | Pn |
| 8 | -CH$_2$CH$_2$CH$_2$- | H | All |
| 9 | -CH$_2$CH$_2$Ch$_2$CH$_2$- | H | Bu |
| 10 | -CH=CH-CH=CH- | H | Pr |
| 11 | -CH=CH-CH=CH- | H | Bu |
| 12 | -CH=CH-CH=CH- | H | Pn |
| 13 | -CH=CH-CH=CH- | H | All |
| 14 | -S-CH=CH- | H | Bu |
| 15 | -S-CH=CH- | H | Pn |

In the above Control compounds No. 6–8, 9, 10–13 and 14–15, $R^{2'}+R^{3'}$ together form a cyclopentane, cyclohexene, benzene or thiophene group, respectively.

The results are shown in Table 14.

TABLE 14

| Compound No. | Acaricidal activity 10 ppm | 3 ppm | Ovicidal activity 10 ppm | 3 ppm |
|---|---|---|---|---|
| 3 | 100 | 86 | 100 | 100 |
| 12 | 100 | 100 | 100 | 100 |
| 50 | 100 | 67 | 100 | 100 |
| 59 | 100 | 70 | 100 | 100 |
| 28 | 100 | 77 | 100 | 100 |
| 51 | 100 | 100 | 100 | 82 |
| 60 | 100 | 81 | 100 | 52 |
| 41 | 100 | 86 | 100 | 100 |
| Control 1 | 73 | 27 | 46 | 20 |
| Control 2 | 100 | 22 | 100 | 24 |
| Control 3 | 64 | 29 | 77 | 23 |
| Control 4 | 94 | 23 | 91 | 14 |
| Control 5 | 40 | 10 | 96 | 20 |
| 154 | 100 | 89 | 100 | 78 |
| 155 | 100 | 79 | 100 | 64 |
| 157 | 100 | 89 | 100 | 76 |
| Control 6 | 70 | 22 | 54 | 15 |
| Control 7 | 69 | 20 | 56 | 14 |
| Control 8 | 43 | 11 | 35 | 8 |
| Control 9 | 77 | 25 | 7 | 0 |
| 160 | 100 | 79 | 100 | 64 |
| 164 | 100 | 100 | 85 | 38 |
| 170 | 100 | 100 | 100 | 58 |
| 174 | 100 | 100 | 69 | 22 |
| 176 | 100 | 91 | 62 | 16 |
| Control 10 | 16 | 0 | 0 | 0 |
| Control 11 | 21 | 0 | 0 | 0 |
| Control 12 | 77 | 15 | 0 | 0 |
| Control 13 | 70 | 22 | 7 | 0 |
| 137 | 100 | 100 | 100 | 78 |
| 143 | 100 | 94 | 100 | 70 |
| 145 | 100 | 100 | 100 | 96 |
| 141 | 100 | 92 | 90 | 42 |
| Control 14 | 75 | 30 | 17 | 0 |
| Control 15 | 48 | 24 | 43 | 13 |
| 78 | 100 | 100 | 100 | 100 |
| 74 | 100 | 100 | 100 | 98 |
| 79 | 100 | 100 | 100 | 100 |
| 80 | 100 | 84 | 100 | 80 |
| 81 | 100 | 100 | 100 | 94 |
| 77 | 100 | 100 | 100 | 95 |
| Control 16 | 34 | 13 | 6 | 0 |
| 88 | 100 | 100 | 100 | 87 |
| 75 | 100 | 100 | 100 | 100 |
| 89 | 100 | 100 | 100 | 61 |
| 90 | 100 | 100 | 100 | 77 |
| 86 | 100 | 100 | 100 | 85 |
| 16 | 100 | 100 | 100 | 94 |
| 87 | 100 | 93 | 100 | 55 |
| Control 17 | 88 | 67 | 39 | 0 |

EXAMPLE 33

Acaricidal activity against adults of the species *Tetranychus urticae*

Test solutions each containing 30 ppm of one of the compounds of the invention in admixture with 0.01% w/v of a spreader were prepared. Cowpea leaves parasitized with adult two-spotted spider mites (*Tetranychus urticae*) were immersed for 10 seconds in the test solutions, air-dried and then left to stand in a room maintained at 25° C.

After 72 hours, the percentage kill was assessed for eact treatment group. A percentage kill of 100% is reported as an acaricidal activity of 5, whilst a percentage kill of from 99 to 80% is reported as an acaricidal activity of 4. All of the compounds of the invention tested killed at least 80% of the mites.

The average number of mites in each treatment group was 50.

The results are shown in Table 15.

TABLE 15

| Compound No. | Acaricidal activity |
|---|---|
| 1 | 4 |
| 2 | 5 |
| 3 | 5 |
| 5 | 5 |
| 7 | 5 |
| 9 | 5 |
| 10 | 4 |
| 11 | 5 |
| 12 | 5 |
| Hydrochloride of 12 | 5 |
| Nitrate of 12 | 5 |
| Phosphate of 12 | 5 |
| Perchlorate of 12 | 5 |
| Phthalate of 12 | 5 |
| p-Toluenesulfonate of 12 | 5 |
| Oxalate of 12 | 5 |
| ½ Malonate of 12 | 5 |
| ½ Fumarate of 12 | 5 |
| Fumarate of 12 | 5 |
| Succinate of 12 | 5 |
| Glutarate of 12 | 5 |
| Adipate of 12 | 5 |
| Maleate of 12 | 5 |
| 13 | 5 |
| 14 | 4 |
| 15 | 5 |
| Hydrochloride of 15 | 5 |
| Oxalate of 15 | 5 |
| 16 | 5 |
| 19 | 5 |
| 20 | 5 |
| 21 | 5 |
| Nitrate of 22 | 5 |
| 23 | 5 |
| 24 | 5 |
| 25 | 5 |
| 26 | 4 |
| 27 | 4 |
| 28 | 5 |
| 29 | 5 |
| 30 | 5 |
| 31 | 5 |
| 32 | 5 |
| 33 | 5 |
| 34 | 5 |
| 35 | 5 |
| 36 | 5 |
| 37 | 5 |
| 38 | 5 |
| 39 | 5 |
| 40 | 5 |
| 41 | 5 |
| 42 | 5 |
| 43 | 5 |
| 44 | 5 |
| 45 | 5 |
| 46 | 4 |
| 47 | 5 |
| 48 | 5 |
| 49 | 4 |
| 50 | 5 |
| 51 | 5 |
| 52 | 4 |
| 53 | 4 |
| 54 | 5 |
| 55 | 5 |
| 56 | 4 |
| 57 | 5 |
| 58 | 5 |
| 59 | 5 |
| 60 | 5 |
| 61 | 5 |
| 62 | 5 |
| 63 | 5 |
| 64 | 5 |
| 65 | 4 |
| 66 | 5 |
| 67 | 5 |
| 68 | 4 |
| 69 | 5 |
| 70 | 5 |
| 71 | 4 |
| 72 | 5 |
| 73 | 5 |
| 74 | 5 |
| 75 | 5 |
| 76 | 4 |
| 77 | 5 |
| 78 | 5 |
| 79 | 5 |
| 80 | 5 |
| 81 | 5 |
| 82 | 5 |
| 83 | 5 |
| 84 | 4 |
| 85 | 4 |
| 86 | 4 |
| 87 | 5 |
| 88 | 4 |
| 89 | 5 |
| 90 | 5 |
| 91 | 5 |
| 92 | 4 |
| 93 | 4 |
| 94 | 4 |
| 95 | 4 |
| 96 | 4 |
| 97 | 4 |
| 98 | 4 |
| 99 | 5 |
| 100 | 5 |
| 101 | 5 |
| 102 | 5 |
| 103 | 4 |
| 104 | 4 |
| 105 | 5 |
| 106 | 4 |
| 107 | 5 |
| 108 | 4 |
| 109 | 5 |
| 110 | 4 |
| 111 | 5 |
| 112 | 5 |
| 113 | 5 |
| 114 | 5 |
| 115 | 5 |
| 116 | 5 |
| 117 | 5 |
| 118 | 5 |
| 119 | 5 |
| 120 | 5 |
| 121 | 5 |
| 122 | 4 |
| 123 | 4 |
| 124 | 5 |
| 125 | 5 |
| 126 | 4 |
| 127 | 5 |
| 128 | 5 |
| 129 | 5 |
| 130 | 5 |
| 132 | 4 |
| 133 | 5 |
| 134 | 5 |
| 135 | 5 |
| 136 | 5 |
| 137 | 5 |
| Hydrochloride of 137 | 5 |
| Nitrate of 137 | 5 |
| Oxalate of 137 | 5 |
| Adipate of 137 | 5 |
| Fumarate of 137 | 5 |
| 138 | 4 |
| 139 | 5 |
| 140 | 5 |
| 141 | 5 |
| 142 | 5 |
| 143 | 5 |
| 144 | 5 |

TABLE 15-continued

| Compound No. | Acaricidal activity |
|---|---|
| 145 | 5 |
| 146 | 5 |
| Oxalate of 146 | 5 |
| 147 | 4 |
| 148 | 4 |
| 149 | 4 |
| 150 | 4 |
| 151 | 4 |
| 152 | 4 |
| 153 | 5 |
| 154 | 5 |
| 155 | 5 |
| 156 | 5 |
| 157 | 5 |
| 158 | 5 |
| 160 | 5 |
| 161 | 5 |
| 162 | 4 |
| 163 | 4 |
| 164 | 5 |
| Hydrochloride of 164 | 5 |
| Nitrate of 164 | 5 |
| Oxalate of 164 | 5 |
| 165 | 5 |
| 166 | 4 |
| 167 | 5 |
| 168 | 5 |
| 169 | 5 |
| 170 | 5 |
| 171 | 5 |
| 172 | 5 |
| 173 | 5 |
| 174 | 5 |
| 175 | 4 |
| 176 | 5 |
| 177 | 4 |
| 178 | 4 |
| 179 | 5 |
| 180 | 5 |
| 181 | 5 |
| 182 | 4 |
| 183 | 5 |
| 184 | 5 |
| 185 | 5 |
| 191 | 5 |
| Oxalate of 191 | 5 |
| Hydrochloride of 191 | 5 |
| Nitrate of 191 | 5 |
| Fumarate of 191 | 5 |
| Adipate of 191 | 5 |
| p-Toluenesulfonate of 191 | 5 |
| 192 | 5 |
| 193 | 5 |
| 194 | 4 |
| 195 | 5 |
| 199 | 5 |
| Oxalate of 199 | 5 |
| Fumarate of 199 | 5 |
| Adipate of 199 | 5 |
| p-Toluenesulfonate of 199 | 5 |
| 203 | 5 |
| Oxalate of 205 | 5 |
| Fumarate of 205 | 5 |
| Adipate of 205 | 5 |
| p-Toluenesulfonate of 205 | 5 |
| 207 | 5 |
| 208 | 4 |
| 222 | 5 |
| Oxalate of 223 | 5 |
| Fumarate of 223 | 5 |
| Adipate of 223 | 5 |
| p-Toluenesulfonate of 223 | 5 |
| 225 | 5 |
| 226 | 5 |
| 227 | 5 |
| 228 | 5 |
| 229 | 5 |
| 230 | 4 |
| 232 | 5 |
| 233 | 4 |
| 234 | 4 |
| 235 | 4 |
| 236 | 5 |
| 237 | 4 |
| 238 | 4 |
| 239 | 5 |
| 240 | 5 |
| 241 | 5 |
| 242 | 4 |
| 243 | 4 |
| 244 | 5 |
| 245 | 4 |
| 246 | 5 |
| 247 | 5 |
| 248 | 5 |
| 249 | 4 |
| 250 | 5 |
| 251 | 4 |

EXAMPLE 34

Ovicidal activity against eggs of the species *Tetranychus urticae*

Test solutions each containing 30 ppm of one of the compounds of the invention in admixture with 0.01% w/v of a spreader were prepared. Cowpea leaves were infected with eggs of the two-spotted spider mite (*Tetranychus urticae*). After infection, the leaves were immersed for 10 seconds in the test solutions, air-dried and then left to stand in a room maintained at 25° C.

After two weeks, the percentage kill was assessed for each treatment group. A percentage kill of 100% is reported as an ovicidal activity of 5, whilst a percentage kill of from 99 to 80% is reported as an ovicidal activity of 4. All of the compounds of the invention tested killed at least 80% of the eggs.

The results are shown in Table 16.

TABLE 16

| Compound No. | Ovicidal Activity |
|---|---|
| 1 | 5 |
| 2 | 5 |
| 3 | 5 |
| 5 | 5 |
| 7 | 5 |
| 9 | 5 |
| 10 | 5 |
| 11 | 5 |
| 12 | 5 |
| Hydrochloride of 12 | 5 |
| Nitrate of 12 | 5 |
| Phosphate of 12 | 5 |
| Perchlorate of 12 | 5 |
| Phthalate of 12 | 5 |
| p-toluenesulfonate of 12 | 5 |
| Oxalate of 12 | 5 |
| ½Malonate of 12 | 5 |
| ½Fumarate of 12 | 5 |
| Fumarate of 12 | 5 |
| Succinate of 12 | 5 |
| Glutarate of 12 | 5 |
| Adipate of 12 | 5 |
| Maleate of 12 | 5 |
| Citrate of 12 | 5 |
| 13 | 5 |
| 14 | 4 |
| 15 | 5 |
| Hydrochloride of 15 | 5 |
| Oxalate of 15 | 5 |
| 16 | 5 |
| 18 | 5 |
| 19 | 5 |
| 20 | 5 |

TABLE 16-continued

| Compound No. | Ovicidal Activity |
|---|---|
| 21 | 5 |
| 22 | 5 |
| Oxalate of 22 | 5 |
| 23 | 5 |
| 24 | 4 |
| 25 | 5 |
| 26 | 5 |
| 27 | 4 |
| 28 | 5 |
| 29 | 5 |
| 30 | 4 |
| 31 | 5 |
| 32 | 5 |
| 33 | 5 |
| 34 | 5 |
| 35 | 5 |
| 36 | 5 |
| 37 | 5 |
| 38 | 5 |
| 39 | 5 |
| 40 | 5 |
| 41 | 5 |
| 42 | 5 |
| 43 | 5 |
| 44 | 5 |
| 45 | 4 |
| 46 | 5 |
| 47 | 5 |
| 48 | 5 |
| 49 | 5 |
| 50 | 5 |
| 51 | 5 |
| 52 | 5 |
| 53 | 5 |
| 54 | 5 |
| 55 | 5 |
| 56 | 5 |
| 57 | 5 |
| 58 | 5 |
| 59 | 5 |
| 60 | 5 |
| 61 | 5 |
| 62 | 5 |
| 63 | 5 |
| 64 | 4 |
| 65 | 4 |
| 66 | 4 |
| 67 | 5 |
| 68 | 4 |
| 69 | 5 |
| 70 | 4 |
| 71 | 4 |
| 72 | 5 |
| 73 | 5 |
| 74 | 5 |
| 75 | 5 |
| 76 | 5 |
| 77 | 5 |
| 78 | 5 |
| 79 | 5 |
| 80 | 5 |
| 81 | 5 |
| 82 | 5 |
| 83 | 5 |
| 84 | 4 |
| 85 | 5 |
| 86 | 4 |
| 87 | 5 |
| 88 | 5 |
| 89 | 5 |
| 90 | 5 |
| 91 | 5 |
| 92 | 5 |
| 93 | 4 |
| 94 | 4 |
| 95 | 4 |
| 96 | 4 |
| 97 | 5 |
| 98 | 5 |
| 99 | 5 |
| 100 | 5 |

TABLE 16-continued

| Compound No. | Ovicidal Activity |
|---|---|
| 101 | 5 |
| 102 | 5 |
| 103 | 4 |
| 104 | 4 |
| 105 | 5 |
| 106 | 4 |
| 107 | 5 |
| 108 | 5 |
| 109 | 5 |
| 110 | 5 |
| 111 | 4 |
| 112 | 4 |
| 113 | 5 |
| 114 | 5 |
| 115 | 5 |
| 116 | 5 |
| 117 | 5 |
| 118 | 5 |
| 119 | 5 |
| 120 | 5 |
| 121 | 5 |
| 122 | 4 |
| 123 | 5 |
| 124 | 5 |
| 125 | 5 |
| 126 | 5 |
| 127 | 5 |
| 128 | 5 |
| 129 | 5 |
| 130 | 5 |
| 132 | 5 |
| 133 | 5 |
| 134 | 5 |
| 135 | 5 |
| 136 | 5 |
| 137 | 5 |
| Hydrochloride of 137 | 5 |
| Nitrate of 137 | 5 |
| Oxalate of 137 | 5 |
| Adipate of 137 | 5 |
| Fumarate of 137 | 5 |
| 138 | 4 |
| 139 | 5 |
| 140 | 4 |
| 141 | 4 |
| 142 | 5 |
| 143 | 5 |
| 144 | 4 |
| 145 | 5 |
| 146 | 5 |
| Oxalate of 146 | 5 |
| 147 | 4 |
| 148 | 4 |
| 149 | 4 |
| 150 | 5 |
| 151 | 5 |
| 152 | 5 |
| 153 | 5 |
| 154 | 5 |
| 155 | 5 |
| 156 | 4 |
| 157 | 5 |
| 158 | 4 |
| 160 | 4 |
| 161 | 5 |
| 162 | 4 |
| 163 | 4 |
| 164 | 4 |
| Hydrochloride of 164 | 5 |
| Nitrate of 164 | 5 |
| Oxalate of 164 | 5 |
| 165 | 4 |
| 166 | 5 |
| 167 | 4 |
| 168 | 4 |
| 169 | 4 |
| 170 | 5 |
| 171 | 4 |
| 172 | 4 |
| 173 | 4 |
| 174 | 5 |

TABLE 16-continued

| Compound No. | Ovicidal Activity |
|---|---|
| 175 | 4 |
| 176 | 4 |
| 177 | 4 |
| 178 | 4 |
| 179 | 4 |
| 180 | 4 |
| 181 | 5 |
| 182 | 4 |
| 183 | 4 |
| 184 | 4 |
| 185 | 5 |
| 191 | 5 |
| Oxalate of 191 | 5 |
| Hydrochloride of 191 | 5 |
| Nitrate of 191 | 5 |
| Fumarate of 191 | 5 |
| Adipate of 191 | 5 |
| p-Toluenesulfonate of 191 | 5 |
| 192 | 5 |
| 193 | 5 |
| 194 | 4 |
| 196 | 5 |
| 199 | 5 |
| Oxalate of 199 | 5 |
| Fumarate of 199 | 5 |
| Adipate of 199 | 5 |
| p-Toluenesulfonate of 199 | 5 |
| 203 | 5 |
| Oxalate of 205 | 5 |
| Fumarate of 205 | 5 |
| Adipate of 205 | 5 |
| p-Toluenesulfonate of 205 | 5 |
| 207 | 5 |
| 208 | 5 |
| 222 | 5 |
| Oxalate of 223 | 5 |
| Fumarate of 223 | 5 |
| Adipate of 223 | 5 |
| p-Toluenesulfonate of 223 | 5 |
| 225 | 5 |
| 226 | 5 |
| 227 | 5 |
| 228 | 5 |
| 229 | 4 |
| 230 | 4 |
| 232 | 4 |
| 233 | 4 |
| 234 | 5 |
| 235 | 4 |
| 236 | 5 |
| 237 | 5 |
| 238 | 5 |
| 239 | 5 |
| 240 | 5 |
| 241 | 5 |
| 242 | 5 |
| 243 | 5 |
| 244 | 5 |
| 245 | 5 |
| 246 | 5 |
| 247 | 5 |
| 248 | 5 |
| 249 | 5 |
| 250 | 5 |
| 251 | 4 |

EXAMPLE 35

Activity against final instar larvae of *Plutella xylostella*

Pieces of cabbage leaf were immersed for 30 seconds in a test solution containing 100 ppm of one of the test compounds shown in Table 17. The leaves were then air-dried and each leaf was placed into a clean plastic ice cream cup of diameter 9 cm. 10 final instar larvae of the diamondback moth (*Plutella xylostella*) were released into each cup, and the emergence inhibition rate was assessed after 120 hours. The tests were conducted in duplicate for each test compound, and the results are shown in Table 17.

TABLE 17

| Compound No. | Emergence inhibition rate (%) |
|---|---|
| 12 | 100 |
| Hydrochloride of 12 | 90 |
| Nitrate of 12 | 90 |
| Phosphate of 12 | 100 |
| p-toluenesulfonate of 12 | 80 |
| Oxalate of 12 | 100 |
| Adipate of 12 | 100 |
| Maleate of 12 | 100 |
| Citrate of 12 | 80 |
| 15 | 90 |
| 16 | 100 |
| 39 | 90 |
| 41 | 80 |
| 47 | 80 |
| 50 | 80 |
| 61 | 80 |
| 69 | 80 |
| 72 | 93 |
| 74 | 100 |
| 75 | 100 |
| 76 | 93 |
| 77 | 100 |
| 78 | 80 |
| 80 | 87 |
| 81 | 80 |
| 88 | 95 |
| 89 | 90 |
| 90 | 100 |
| 91 | 85 |
| 97 | 100 |
| 99 | 100 |
| 101 | 100 |
| 107 | 93 |
| 110 | 90 |
| 113 | 80 |
| 114 | 80 |
| 118 | 89 |
| Nitrate of 137 | 80 |
| Oxalate of 137 | 95 |
| Adipate of 137 | 100 |
| Maleate of 137 | 100 |
| 141 | 90 |
| 145 | 90 |
| 148 | 80 |
| 149 | 90 |
| 155 | 80 |
| 164 | 80 |
| Hydrochloride of 164 | 80 |
| 169 | 100 |
| 170 | 80 |
| 171 | 90 |
| 179 | 90 |
| 182 | 80 |
| 198 | 90 |
| 199 | 100 |
| 204 | 90 |
| 205 | 90 |
| 206 | 90 |
| 209 | 90 |
| 213 | 90 |
| 220 | 90 |
| 223 | 90 |
| 228 | 90 |
| 234 | 87 |
| 236 | 100 |
| 240 | 80 |
| 241 | 93 |
| 242 | 82 |
| 243 | 100 |
| 244 | 100 |
| 246 | 100 |
| 248 | 87 |

EXAMPLE 36

Activity against *Myzus persicae*

Test solutions, each containing 50 ppm of one of the test compounds shown in Table 18, were sprayed onto leaves of a cabbage parasitized by the green peach aphid (*Myzus persicae*), at the rate of 10 ml per leaf. Each leaf was placed by its leafstalk in a 30 ml bottle containing water, and the mouth of the bottle was plugged with cotton wool. The bottles awere then left in a room maintained at 25° C. After 72 hours, the percentage mortality of the aphids was assessed. The results are shown in Table 18.

TABLE 18

| Compound No. | Mortality (%) |
|---|---|
| 1 | 95 |
| 2 | 99 |
| 3 | 99 |
| 5 | 86 |
| 6 | 89 |
| 7 | 99 |
| 12 | 100 |
| Nitrate of 12 | 93 |
| Oxalate of 12 | 99 |
| Adipate of 12 | 89 |
| Maleate of 12 | 99 |
| 28 | 91 |
| 30 | 90 |
| 36 | 87 |
| 37 | 84 |
| 50 | 85 |
| 51 | 85 |
| 63 | 85 |
| 74 | 100 |
| 78 | 100 |
| 79 | 97 |
| 80 | 91 |
| 81 | 98 |
| 88 | 100 |
| 90 | 82 |
| 91 | 99 |
| 97 | 100 |
| 99 | 85 |
| 100 | 95 |
| 109 | 97 |
| 113 | 97 |
| Oxalate of 137 | 96 |
| Adipate of 137 | 89 |
| Maleate of 137 | 99 |
| 191 | 97 |
| Nitrate of 191 | 93 |
| Oxalate of 191 | 90 |
| 199 | 100 |
| 202 | 92 |
| 208 | 90 |
| 211 | 94 |
| 213 | 97 |
| 228 | 100 |
| 239 | 97 |
| 244 | 84 |

We claim:

1. A compound of formula (I):

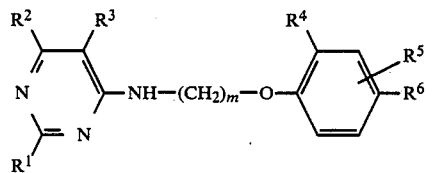

in which:
$R^1$ represents a hydrogen atom, a $C_1$-$C_4$ alkyl group or a halogen atom;

$R^2$ and $R^3$ are independently selected from the group consisting of $C_1$-$C_4$ alkyl groups, halogen atoms, $C_2$-$C_4$ alkoxyalkyl groups, $C_2$-$C_4$ alkylthioalkyl groups and $C_3$ and $C_4$ cycloalkyl groups, or $R^2$ and $R^3$ together represent, with the carbon atoms to which they are attached, a 5- or 6-membered ring which is a (i) saturated carbocyclic ring or (ii) an unsaturated carbocyclic ring having one or two double bonds, or is a heterocyclic ring containing a single oxygen or sulfur hetero-atom, the ring being unsubstituted or having 1 or 2 substituents selected from the group consisting of $C_1$-$C_4$ alkyl groups and halogen atoms;

m is 2 or 3;

$R^4$ and $R^5$ are independently selected from the group consisting of hydrogen atoms, $C_1$-$C_4$ alkyl groups and halogen atoms; and $R^6$ represents a group of formula —A—B—(-DO)$_n$—E, where
A represents a $C_1$-$C_8$ alkylene group or a $C_1$-$C_8$ alkylene group having a single $C_1$-$C_4$ alkoxy substituent;
B represents an oxygen atom, a sulfur atom or an imino group;
D represents a $C_1$-$C_6$ alkylene group or an alkyleneoxyalkylene group where each alkylene part is $C_1$-$C_4$;
n is 0 or 1; and
E represents a $C_1$-$C_6$ alkyl group, a $C_3$-$C_6$ alkenyl group, a $C_4$-$C_6$ alkadienyl group, a $C_3$ or $C_4$ alkynyl group or phenylalkyl group having from 7 to 9 carbon atoms;
or a group of formula —CH$_2$—W, where:
W represents a group of formula —CH=N—OR$^7$ where R$^7$ represents a hydrogen atom, a $C_1$—$C_4$ alkyl group, a $C_3$ or $C_4$ alkenyl group or a $C_7$-$C_9$ phenylalkyl group,
a morpholinomethyl group or a heterocyclic group selected from the group consisting of

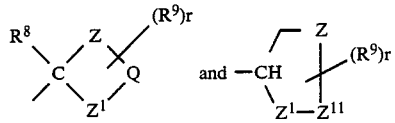

in which:
Z and Z' are independently selected from the group consisting of oxygen atoms and sulfur atoms;
Z" represents a group of formula >CH$_2$ or >S→(O)$_s$, in which s is 0, 1 or 2;
Q represents an alkylene or alkenylene group having from 2 to 5 carbon atoms;
$R^8$ represents a hydrogen atom or a $C_1$-$C_4$ alkyl group;
$R^9$ represents a $C_1$-$C_4$ alkyl group, a $C_1$-$C_4$ haloalkyl group or a phenyl group; and
r is 0, 1 or 2;
or an acid salt thereof.

2. The compound as claimed in claim 1, in which $R^1$ represents a hydrogen atom or a methyl group.

3. The compound as claimed in claim 1, in which one of $R^2$ and $R^3$ represents a methyl or ethyl group, and the other represents a methyl group, an ethyl group, a chlorine atom or a bromine atom.

4. The compound as claimed in claim 1, in which $R^2$ and $R^3$ together form a cyclopentene, cyclohexene, benzene or thiophene ring fused to the pyrimidine ring, said rings being unsubstituted or said cyclopentene, cyclohexene and benzene rings having 1 or 2 substituents selected from the group consisting of methyl, chlorine and fluorine substituents, or said thiophene ring having one or two methyl substituents.

5. The compound as claimed in claim 1, in which $R^4$ represents a hydrogen atom, a methyl group or an ethyl group.

6. The compound as claimed in claim 1, in which $R^5$ represents a hydrogen atom, a chlorine atom or a methyl group.

7. The compound as claimed in claim 1, in which m is 2.

8. The compound as claimed in claim 1, in which $R^6$ represents a group of formula $-A-B-(DO)_n-E$, in which A represents an alkylene group having from 1 to 5 carbon atoms, said alkylene group being unsubstituted or having a single methoxy substituent.

9. The compound as claimed in claim 1, wherein $R^6$ represents a group of formula $-A-B-(DO)_n-E$ in which $-B-(DO)_n-$ represents an oxygen atom, a sulfur atom, an imino group or a group of formula $-NH-(CH_2)_2-O-$, $-O-(CH_2)_p-O-$ or $-O-(CH_2)_q-O-(CH_2)_q-O-$ (in which p is an integer from 1 to 3 and q is 1 or 2).

10. The compound as claimed in claim 1, in which $R^6$ represents a group of formula $-A-B-(DO)_n-E$, in which E represents a $C_1-C_4$ alkyl group, a $C_3$ or $C_4$ alkenyl group, a propynyl group or a benzyl group.

11. The compound as claimed in claim 1, in which $R^6$ represents a group of formula $-CH_2-CH=N-OR^7$, in which $R^7$ represents a $C_1-C_4$ alkyl group, an allyl group or a benzyl group.

12. The compound as claimed in claim 1, in which $R^6$ represents a group of formula $-CH_2-W$, in which W represents a group of formula

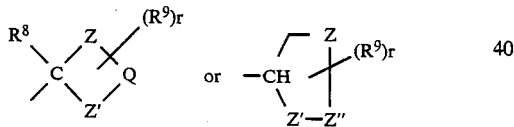

in which:
Z and Z' are independently selected from the group consisting of oxygen atoms and sulfur atoms;
Q represents an alkylene or alkenylene group having from 2 to 5 carbon atoms;
$R^8$ represents a hydrogen atom or a $C_1-C_4$ alkyl group;
$R^9$ represents a $C_1-C_4$ alkyl group, a $C_1-C_4$ haloalkyl group or a phenyl group;
r is 0, 1 or 2;
Z" represents a group of formula $>CH_2$ or $>S \rightarrow (O)_s$; and
s is 0, 1 or 2.

13. A compound as claimed in claim 1, in which:
$R^1$ represents a hydrogen atom or a methyl group;
one of $R^2$ and $R^3$ represents a methyl or ethyl group and the other represents a methyl group, an ethyl group, a chlorine atom or a bromine atoms, or $R^2$ and $R^3$ together form a cyclopentene, cyclohexene, benzene or thiophene ring fused to the pyrimidine ring, said rings being unsubstituted or said cyclopentene, cyclohexene and benzene rings having one or two substituents selected from the group consisting of methyl, chlorine and fluorine substituents or said thiophene ring having one or two methyl substituents;
m is 2;
$R^4$ represents a hydrogen atom, a methyl group or an ethyl group;
$R^5$ represents a hydrogen atom, a chlorine atom or a methyl group;
$R^6$ represents a group of the formula $-A-B(-DO)_n-E$, and
A represents a $C_1-C_5$ alkylene group or a $C_1-C_5$ alkylene group having a single methoxy substituent;
$-B-(DO)_n-$ represents an oxygen atom, a sulfur atom, an imino group or a group of formula $-NH-(CH_2)_2-O-$, $-O-(CH_2)_p-O-$ or $-O(CH_2)_q-O-(CH_2)_q-O-$ (in which p is an integer from 1 to 3 and q is 1 or 2).

14. The compound as claimed in claim 1, in which:
$R^1$ represents a hydrogen atom or a methyl group;
one of $R^2$ and $R^3$ represents a methyl or ethyl group and the other represents a chlorine atom or a bromine atom, or $R^2$ and $R^3$ form a benzene or thiophene ring fused with the pyrimidine ring;
$R^4$ represents a methyl group;
$R^5$ represents a hydrogen atom; and
$R^6$ represents a group of formula $-CH_2-CH=N-OR^7$, in which $R^7$ represents an ethyl group or an allyl group.

15. The compound as claimed in claim 1, in which:
$R^1$ represents a hydrogn atom or a methyl group;
one of $R^2$ and $R^3$ represents a methyl or ethyl group and the other represents a chlorine atom or a bromine atom, or $R^2$ and $R^3$ form a benzene or thiophene ring fused with the pyrimidine ring;
$R^4$ represents a methyl group;
$R^5$ represents a hydrogen atom; and
$R^6$ represents a group of formula $-CH_2-W$ in which W represents a group of formula

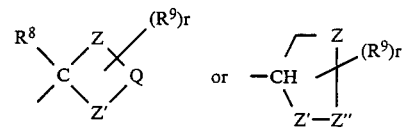

Z and Z' are independently selected from the group consisting of oxygen atoms and sulfur atoms;
Q represents an alkylene or alkenylene group having from 2 to 5 carbon atoms;
Z" represents a group of formula $>CH_2$ or $>S \rightarrow (O)_s$;
$R^8$ represents a hydrogen atom or a methyl group;
$R^9$ represents a methyl group, an ethyl group or a chloromethyl group;
and r is 0, 1 or 2.

16. The compounds of claim 1 which are 5-chloro-4-{2-[4-(2-ethoxyethyl)-2-methylphenoxy]ethylamino}-6-methylpyrimidine or an acid addition salt thereof.

17. The compounds of claim 1 which are 5-chloro-4-{2-[4-(2-ethoxyethyl)-2,3-dimethylphenoxy]ethylamino}-6-ethylpyrimidine or an acid addition salt thereof.

18. The compounds of claim 1 which are 5-bromo-4-{2-[4-(2-ethoxyethyl)-2-methylphenoxy]ethylamino}-6-ethylpyrimidine or an acid addition salt thereof.

19. An agrochemical composition comprising an effective amount of an insecticidal and acaricidal agent and a carrier therefor, wherein said agent is selected from the group consisting of compounds of formula (I):

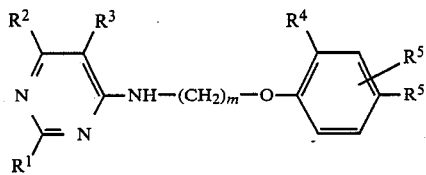

in which:

R$^1$ represents a hydrogen atom, a C$_1$-C$_4$ alkyl group or a halogen atom;

R$^2$ and R$^3$ are independently selected from the group consisting of C$_1$-C$_4$ alkyl groups, halogen atoms, C$_2$-C$_4$ alkoxyalkyl groups, C$_2$-C$_4$ alkylthioalkyl groups and C$_3$ and C$_4$ cycloalkyl groups, or R$^2$ and R$^3$ together represent, with the carbon atoms to which they are attached, a 5- or 6-membered ring which is a (i) saturated carbocyclic ring or (ii) an unsaturated carbocyclic ring having one or two double bonds, or is a heterocyclic rig containing a single oxygen or sulfur hetero-atom, the ring being unsubstituted or having 1 or 2 substituents selected from the group consisting of C$_1$-C$_4$ alkyl groups and halogen atoms;

m is 2 or 3;

R$^4$ and R$^5$ are independently selected from the group consisting of hydrogen atoms, C$_1$-C$_4$ alkyl groups and halogen atoms; and R$^6$ represents a group of formula —A—B—(-DO)$_n$—E, where A represents a C$_1$-C$_8$ alkylene group or a C$_1$-C$_8$ alkylene group having a single C$_1$-C$_4$ alkoxy substituent;

B represents an oxygen atom, a sulfur atom or an imino group;

D represents a C$_1$-C$_6$ alkylene group or an alkyleneoxyalkylene group where each alkylene part is C$_1$-C$_4$;

n is 0 or 1; and

E represents a C$_1$-C$_6$ alkyl group, a C$_3$-C$_6$ alkenyl group, a C$_4$-C$_6$ alkadienyl group, a C$_3$ or C$_4$ alkynyl group or phenylalkyl group having from 7 to 9 carbon atoms;

or a group of formula —CH$_2$—W, where:

W represents a grop of formula —CH=N—OR$^7$ where R$^7$ represents a hydrogen atom, a C$_1$-C$_4$ alkyl group, a C$_3$ or C$_4$ alkenyl group or a C$_7$-C$_9$ phenylalkyl group, a morpholinomethyl group or a heterocyclic group selected from the group consisting of

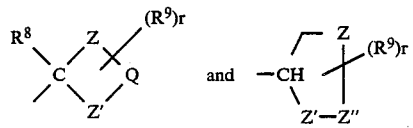 and in which:

Z and Z' are independently selected from the group consisting of oxygen atoms and sulfur atoms;

Z" represents a group of formula >CH$_2$ or >S→(O)$_s$, in which s is 0, 1 or 2;

Q represents an alkylene or alkenylene group having from 2 to 5 carbon atoms;

R$^8$ represents a hydrogen atom or a C$_1$-C$_4$ alkyl group;

R$^9$ represents a C$_1$-C$_4$ alkyl group, a C$_1$-C$_4$ haloalkyl group or a phenyl group; and r is 0, 1 or 2;

or an acid addition salt thereof.

20. The composition as claimed in claim 19, in which R$^1$ represents a hydrogen atom or a methyl group.

21. The composition as claimed in claim 19, in which one of R$^2$ and R$^3$ represents a methyl or ethyl group, and the other represents a methyl group, an ethyl group, a chlorine atom or a bromine atom.

22. The composition as claimed in claim 19, in which R$^2$ and R$^3$ together form a cyclopentene, cyclohexene, benzene or thiophene ring fused to the pyrimidine ring, said rings being unsubstituted or said cyclopentene, cyclohexene and benzene rings having 1 or 2 substituents selected from the group consisting of methyl, chlorine and fluorine substituents, or said thiophene ring having one or two methyl substituents.

23. The composition as claimed in claim 19, in which R$^4$ represents a hydrogen atom, a methyl group or an ethyl group.

24. The composition as claimed in claim 19, in which R$^5$ represents a hydrogen atom, a chlorine atom or a methyl group.

25. The composition as claimed in claim 19, in which m is 2.

26. The composition as claimed in claim 19, in which R$^6$ represents a group of formula —A—B—(DO)$_n$—E, in which A represents an alkylene group having from 1 to 5 carbon atoms, said alkylene group being unsubstituted or having a single methoxy substituent.

27. The composition as claimed in claim 19, wherein R$^6$ represents a group of formula —A—B—(DO)$_n$—E in which —B—(DO)$_n$— represents an oxygen atom, a sulfur atom, an imino group or a group of formula —NH—(CH$_2$)$_2$—O—, —O—(CH$_2$)$_p$—O— or —O—(CH$_2$)$_q$—O—(CH$_2$)$_q$—O— (in which p is an integer from 1 to 3 and q is 1 or 2).

28. The composition as claimed in claim 19, in which R$^6$ represents a group of formula —A—B—(DO)$_n$—E, in which E represents a C$_1$-C$_4$ alkyl group, a C$_3$ or C$_4$ alkenyl group, a propynyl group or a benzyl group.

29. The composition as claimed in claim 19, in which R$^6$ represents a group of formula —CH$_2$—CH=N—OR$^7$, in which R$^7$ represents a C$_1$-C$_4$ alkyl group, an allyl group or a benzyl group.

30. The composition as claimed in claim 19, in which R$^6$ represents a group of formula —CH$_2$—W, in which W represents a group of formula

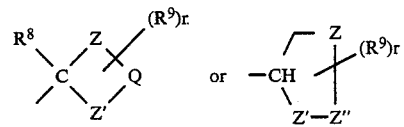

in which:

Z and Z' are independently selected from the group consisting of oxygen atom and sulfur atoms;

Q represents an alkylene or alkenylene group having from 2 to 5 carbon atoms;

R$^8$ represents a hydrogen atom or a C$_1$-C$_4$ alkyl group;

R⁹ represents a C₁–C₄ alkyl group, a C₁–C₄ haloalkyl group or a phenyl group;
r is 0, 1 or 2;
Z" represents a group of formula >CH₂ or >S→(O)ₛ; and
s is 0, 1 or 2.

31. A composition as claimed in claim 19, in which
R¹ represents a hydrogen atom or a methyl group;
one of R² and R³ represents a methyl or ethyl group and the other represents a methyl group, an ethyl group, a chlorine atom or a bromine atom, or R² and R³ together form a cyclopentene, cyclohexane, benzene or thiophene ring fused to the pyrimidine ring, said rings being unsubstituted or said cyclopentene, cyclohexene and benzene rings having one or two substituents selected from the group consisting of methyl, chlorine and fluorine substituents or said thiophene ring having one or two methyl substituents;
m is 2;
R⁴ represents a hydrogen atom, a methyl group or an ethyl group;
R⁵ represents a hydrogen atom, a chlorine atom or a methyl group;
R⁶ represents a group of the formula —A—B(-DO)ₙ—E, and
A represents a C₁–C₅ alkylene group or a C₁–C₅ alkylene group having a single methoxy substituent;
—B—(DO)ₙ— represents an oxygen atom, a sulfur atom, an imino group or a group of formula —NH—(CH₂)₂—O—, —O—(CH₂)ₚ—O— or —O(CH₂)_q—O—(CH₂)_q—O— (in which p is an integer from 1 to 3 and q is 1 or 2).

32. The composition as claimed in claim 19, in which:
R¹ represents a hydrogen atom or a methyl group;
one of R² and R³ represents a methyl or ethyl group and the other represents a chlorine atom or a bromine atom, or R² and R³ form a benzene or thiophene ring fused with the pyrimidine ring;
R⁴ represents a methyl group;
R⁵ represents a hydrogen atom; and
R⁶ represents a group of formula —CH₂—CH=N—OR⁷, in which R⁷ represents an ethyl group or an allyl group.

33. The composition as claimed in claim 19, in which:
R¹ represents a hydrogen atom or a methyl group;
one of R² and R³ represents a methyl or ethyl group and the other represents a chlorine atom or a bromine atom, or R² and R³ form a benzene or thiophene ring fused with the pyrimidine ring;
R⁴ represents a methyl group;
R⁵ represents a hydrogen atom; and
R⁶ represents a group of formula —CH₂—W in which W represents a group of formula

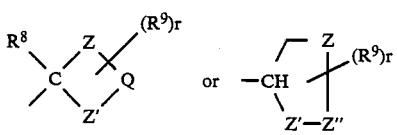

Z and Z' are independently selected from the group consisting of oxygen atoms and sulfur atoms;
Q represents an alkylene or alkenylene group having from 2 to 5 carbon atoms;
Z" represents a grou of formula >CH₂ or >S→(O)ₛ;

R⁸ represents a hydrogen atom or a methyl group;
R⁹ represents a methyl group, an ethyl group or a chloromethyl group;
and r is 0, 1 or 2.

34. The composition as claimed in claim 19, wherein said agent is selected from the group consisting of:
5-chloro-4-{2-[4-(2-ethoxyethyl)-2-methylphenoxy]ethylamino}-6-methylpyrimidine
5-chloro-4-{2-[4-(2-ethoxyethyl)-2,3-dimethylphenoxy]ethylamino}-6-ethylpyrimidine
5-bromo-4-{2-[4-(2-ethoxyethyl)-2-methylphenoxy]ethylamino}-6-ethylpyrimidine
or an acid addition salt thereof.

35. A method of protecting plants from insect and acarid attack, comprising applying to the site of said plants an agricultural composition which contains as an active ingredient an insectically and acaricidally effective amount of a compound of formula (I), as claimed in claim 1, or an acid addition salt thereof.

36. The compound as claimed in claim 1, wherein
R⁶ is a group of the formula —CH₂—W₁, W is a heterocyclic group, and
Q is selected from the group consisting of ethylene, trimethylene, tetramethylene, pentamethylene, vinylene, propenylene, 1-butenylene and 2-butenylene group;
R⁸ is selected from the group consisting of hydrogen, methyl, ethyl, propyl and butyl;
R⁹ is selected from the group consisting of methyl, ethyl, propyl, chloromethyl, bromomethyl, fluoromethyl, iodomethyl, dichloromethyl, trifluoromethyl, 2-chloroethyl, 2,2-dichloroethyl, pentabromoethyl, 3-fluoropropyl, 2,3-dibromobutyl, and phenyl.

37. The compound as claimed in claim 15, wherein
R⁶ is a group of the formula —CH₂—W₁, W is a heterocyclic group, and
Q is selected from the group consisting of ethylene, trimethylene, tetramethylene, pentamethylene, vinylene, propenylene, 1-butenylene and 2-butenylene group;
R⁸ is selected from the group consisting of hydrogen, methyl, ethyl, propyl and butyl;
R⁹ is selected from the group consisting of methyl, ethyl, propyl, chloromethyl, bromomethyl, fluoromethyl, iodomethyl, dichloromethyl, trifluoromethyl, 2-chloroethyl, 2,2-dichloroethyl, pentabromoethyl, 3-fluoropropyl, 2,3-dibromobutyl, and phenyl.

38. The compound as claimed in claim 1, wherein R⁶ is a group of the formula —CH₂—W, and W is a substituted or unsubstituted heterocyclic selected from the group consisting of 1,3-dioxolan-2-yl, 1,3-oxathiolan-2-yl, 1,3-dithiolan-2-yl, 1,4-dioxolan-2-yl, 1,3,2-dioxathiolan-4-yl, 1,3-dioxan-2-yl, 1,3-dioxepan-2-yl, 4,7-dihydro-1,3-dioxepin-2-yl and 1,3-dioxecan-2-yl.

39. The compound as claimed in claim 15, wherein R⁶ is a group of the formula —CH₂—W, and W is a substituted or unsubstituted heterocyclic selected from the group consisting of 1,3-dioxolan-2-yl, 1,3-oxathiolan-2-yl, 1,3-dithiolan-2-yl, 1,4-dioxolan-2-yl, 1,3,2-dioxathiolan-4-yl, 1,3-dioxan-2-yl, 1,3-dioxepan-2-yl, 4,7-dihydro-1,3-dioxepin-2-yl and 1,3-dioxecan-2-yl.

40. The composition as claimed in claim 19, wherein
R⁶ is a group of the formula —CH₂—W₁, W is a heterocyclic group, and
Q is selected from the group consisting of ethylene, trimethylene, tetramethylene, pentamethylene, vinylene, propenylene, 1-butenylene and 2-butenylene group;

$R^8$ is selected from the group consisting of hydrogen, methyl, ethyl, propyl and butyl;

$R^9$ is selected from the group consisting of methyl, ethyl, propyl, chloromethyl, bromomethyl fluoromethyl, iodomethyl, dichloromethyl, trifluoromethyl, 2-chloroethyl, 2,2-dichloroethyl, pentabromoethyl, 3-fluoropropyl, 2,3-dibromobutyl, and phenyl.

41. The composition as claimed in claim 33, wherein $R^6$ is a group of the formula —$CH_2$—$W_1$, W is a heterocyclic group, and Q is selected from the group consisting of ethylene, trimethylene, tetramethylene, pentamethylene, vinylene, propenylene, 1-butenylene and 2-butenylene group;

$R^8$ is selected from the group consisting of hydrogen, methyl, ethyl, propyl and butyl;

$R^9$ is selected from the group consisting of methyl, ethyl, propyl, chloromethyl, bromomethyl, fluoromethyl, iodomethyl, dichloromethyl, trifluoromethyl, 2-chloroethyl, 2,2-dichloroethyl, pentabromoethyl, 3-fluoropropyl, 2,3-dibromobutyl, and phenyl.

42. The composition as claimed in claim 19, wherein $R^6$ is a group of the formula —$CH_2$—W, and W is a substituted or unsubstituted heterocyclic selected from the group consisting of 1,3-dioxolan-2-yl, 1,3-oxathiolan-2-yl, 1,3-dithiolan-2-yl, 1,4-dioxolan-2-yl, 1,3,2-dioxathiolan-4-yl, 1,3-dioxan-2-yl, 1,3-dioxepan-2-yl, 4,7-dihydro-1,3-dioxepin-2-yl and 1,3-dioxecan-2-yl.

43. The composition as claimed in claim 33, wherein $R^6$ is a group of the formula —$CH_2$—W, and W is a substituted or unsubstituted heterocyclic selected from the group consisting of 1,3-dioxolan-2-yl, 1,3-oxathiolan-2-yl, 1,3-dithiolan-2-yl, 1,4-dioxolan-2-yl, 1,3,2-dioxathiolan-4-yl, 1,3-dioxan-2-yl, 1,3-dioxepan-2-yl, 4,7-dihydro-1,3-dioxepin-2-yl and 1,3-dioxecan-2-yl.

* * * * *